US008389749B2

(12) United States Patent
Dumesic et al.

(10) Patent No.: US 8,389,749 B2
(45) Date of Patent: Mar. 5, 2013

(54) METHOD TO PRODUCE, RECOVER AND CONVERT FURAN DERIVATIVES FROM AQUEOUS SOLUTIONS USING ALKYLPHENOL EXTRACTION

(75) Inventors: James Dumesic, Verona, WI (US); David Alonso, Madison, WI (US); Jesse Bond, Madison, WI (US); Thatcher Root, Madison, WI (US); Mei Chia, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 103 days.

(21) Appl. No.: 13/115,439

(22) Filed: May 25, 2011

(65) Prior Publication Data

US 2012/0302765 A1 Nov. 29, 2012

(51) Int. Cl.
*C07D 307/33* (2006.01)
*C07D 307/48* (2006.01)
*C07D 307/44* (2006.01)
*C07D 307/46* (2006.01)
*C07C 69/716* (2006.01)
*C07C 59/185* (2006.01)

(52) U.S. Cl. ........ 549/489; 549/326; 549/488; 549/503; 560/174; 562/577

(58) Field of Classification Search .................. 549/326, 549/489, 503, 488; 560/174; 562/577
See application file for complete search history.

(56) References Cited

U.S. PATENT DOCUMENTS

| 5,608,105 A | 3/1997 | Fitzpatrick |
| 2008/0033188 A1 | 2/2008 | Dumesic et al. |
| 2010/0312006 A1 | 12/2010 | Lake et al. |

FOREIGN PATENT DOCUMENTS

| JP | 3337326 A | 10/2002 |
| WO | WO 2009/130386 A1 | 10/2009 |

OTHER PUBLICATIONS

Alonso et al., Catalytic conversion of biomass to biofuels, *Green Chem.* 12, 1493-1513 (2010).
Bond et al., Integrated Catalytic Conversion of γ-Valerolactone to Liquid Alkenes for Transportation Fuels, *Science* 327, 1110-1114 (2010).
Bozell et al., Production of levulinic acid and use as a platform chemical for derived products, *Resour. Conserv. Recy.* 28, 227-239 (2000).
Bozell et al., Technology development for the production of biobased products from biorefinery carbohydrates—the US Department of Energy's "Top 10" revisited, *Green Chem.* 12, 539-554 (2010).
Bozell, J.J., Connecting Biomass and Petroleum Processing with a Chemical Bridge, *Science* 329, 522-523 (2010).
Braden, D.J., Thesis—Catalytic conversion of Lignocellulosic Biomass into Liquid Transportation Fuels: Fundamental and Applied Approaches, UW-Madison (2010).
Deng et al., Catalytic Conversion of Biomass-Derived Carbohydrates into γ- Valerolactone without Using an External $H_2$ Supply, *Angew. Chem. Int. Ed.* 48, 6529-6532 (2009).
Fegyverneki et al., Gamma-valerolactone-based solvents, *Tetrahedron* 66, 1078-1081 (2010).
Fellay et al., A Viable Hydrogen-Storage System Based On Selective Formic Acid Decomposition with a Ruthenium Catalyst, *Angew. Chem. Int. Edit.* 47, 3966-3968 (2008).
Geilen et al., Selective and Flexible Transformation of Biomass-Derived Platform Chemicals by a Multifunctional Catalytic System, *Angew. Chem. Inter. Ed.* 49, 5510-5514 (2010).
Heeres et al., Combined dehydration/(transfer)-hydrogenation of C6-sugars (D-glucose and D-fructose) to γ-valerolactone using ruthenium catalysts, *Green Chem.* 11, 1247-1255 (2009).
Horvat et al., Mechanism of Levulinic Acid Formation, *Tetrahedron Lett.* 26, No. 17, 2111-2114 (1985).
Horvath et al., γ-Valerolactone—a sustainable liquid for energy and carbon-based chemicals, *Green Chem.* 10, 238-242 (2008).
Huber et al., Raney Ni-Sn Catalyst for $H_2$ Production from Biomass-Derived Hydrocarbons, *Science* 300, 2075-2077 (2003).
Kirk-Othmer Encyclopedia of Chemical Technology (Ed Wiley, New York 2000), Alkylphenols, vol. 2, pp. 203-232.
Kunkes et al., Catalytic Conversion of Biomass to Monofunctional Hydrocarbons and Targeted Liquid-fuel Classes, *Science* 322, 417-421 (2008).
Lange et al., Towards "bio-based" Nylon: conversion of γ-valerolactone to methyl pentenoate under catalytic distillation conditions, *Chem. Commun.*, 3488-3490 (2007).
Lange et al., Valeric Biofuels: A Platform of Cellulosic Transportation Fuels, *Angew. Chem. Inter. Ed.* 49, 4479-4483 (2010).
Liu et al., The Effect if Flow Rate of Compressed Hot Water on Xylan, Lignin, and Total Mass Removal from Corn Stover, *Ind. Eng. Chem. Resear.* 42, 5409-5416 (2003).
Mehdi et al., Integration of Homogeneous and Heterogeneous Catalytic Processes for a Multi-step Conversion of Biomass: From Sucrose to Levulinic Acid, γ-Valerolactone, 1,4-Pentanediol, 2-methyl-tetrahydrofuran, and Alkanes, *Top. Catal.* 48, 49-54 (2008).
Prairie et al., A Fourier Transform Infrared Spectroscopic Study of $CO_2$ Methanation on Supported Ruthenium, *J. Catal.* 129, 130-144 (1991).
Riguetto et al., Ru-Sn catalysts for selective hydrogenation of crontonaldehyde: Effect of the Sn/(Ru+Sn) ratio, *Appl .Catal. Gen.* 318, 70-78 (2007).
Serrano-Ruiz et al., Conversion of cellulose to hydrocarbon fuels by progressive removal of oxygen, *Appl. Catal. B-Environ.* 100, 184-189 (2010).
Springerova et al., Selective hydrogenation of α,β-unsaturated carbonyl compounds on supported Ru-Sn catalysts, *Res. Chem. Intermediat.* 31, 785-795 (2005).
Yan et al., Synthesis of γ-Valerolactone by Hydrogenation of Biomass-derived Levulinic Acid over Ru/C Catalyst, *Energ. fuel* 23, 3853-3858 (2009).
Hackenberger, Christian, "Stichwort Alkylphenole,", ROMPP Online, Version 3.26, Georg Thieme Verlag, Nov. 2010, XP002681849, Retrieved from the Internet: URL:http://www.roempp.com/prod/ [retrieved on Aug. 13, 2012].
Alonso, David Martin, et al., "Production of Biofuels from Cellulose and Corn Stover Using Alkylphenol Solvents," Chemsuschem, vol. 4, No. 8, pp. 1078-1081, Aug. 22, 2011.
Gurbuz, Elif I., et al., "Conversion of Hemicellulose to Furfural and Levulinic Acid using Biphasic Reactors with Alkylphenol Solvents," Chemsuschem, vol. 5, No. 2, pp. 383-387, Feb. 13, 2012.

*Primary Examiner* — B. Dentz
(74) *Attorney, Agent, or Firm* — Joseph T. Leone, Esq.; DeWitt Ross & Stevens S.C.

(57) ABSTRACT

Described is a catalytic process for converting biomass to furan derivatives (e.g., furfural, furfuryl alcohol, etc.) using a biphasic reactor containing a reactive aqueous phase and an organic extracting phase containing an alkylphenol. The process provides a cost-effective route for producing furfural, furfuryl alcohol, levulinic acid hydroxymethylfurfural, γ-valerolactone, and the like. The products formed are useful as value-added intermediates to produce polymers, as precursors to diesel fuel, and as fuel additives.

31 Claims, 16 Drawing Sheets

METHOD TO PRODUCE, RECOVER AND CONVERT FURAN DERIVATIVES FROM AQUEOUS SOLUTIONS USING ALKYLPHENOL EXTRACTION

FEDERAL FUNDING STATEMENT

This invention was made with government support under W911NF-09-2-0010 awarded by the ARMY/ARO. The government has certain rights in the invention.

FIELD OF THE INVENTION

The invention is directed to a method for selectively dehydrating carbohydrates, (preferably sugars, e.g., fructose, glucose, xylose) to yield furanic compounds such as hydroxymethylfurfural and/or furfural, and methods to process these products further to yield derivatives such as furfuryl alcohol, levulinic acid, levulinic esters and/or γ-valerolactone. The method may use one or more two-phase reactors wherein the sugar is dehydrated in an aqueous phase (preferably using an acid catalyst such as a strong acid or an acidic ion-exchange resin). Preferably, the products are continuously extracted into an organic phase comprising an alkylphenol and may be isolated as a final product or upgraded in a variety of cascades described herein.

BACKGROUND

Since at least as early as the mid-1960's, scientific and economic forecasters have been predicting an approaching era of diminishing availability of petrochemical resources to produce the energy and chemical materials needed by industrialized societies. On one hand, discoveries of new petroleum reserves and new petroleum production technologies (e.g., deep-water, off-shore drilling) have staved off an economically catastrophic shortage of crude oil. On the other hand, rapidly industrializing national economies (most notably China and India), coupled with political instability in petroleum-producing regions (most notably the Middle East, Nigeria, and Venezuela), have pushed oil prices to record levels. In January of 1999, crude oil cost $17 per barrel. By early 2006, the price of a barrel of crude oil topped $70 for the first time in history. In March of 2008, the price of a barrel of crude oil topped $110, on its way to an all-time peak of $147 per barrel in July of 2008. As of May 2011, the spot price of a barrel of crude oil is hovering at slightly over $100 per barrel. Environmental, ecological, and political considerations have also effectively made certain proven reserves of petroleum off-limits to commercial exploitation. For example, production of petroleum from proven reserves in the Arctic National Wildlife Refuge in Alaska has been (and for the foreseeable future, will continue to be) blocked by federal and state legislation to preserve this unique natural landscape from human encroachment. Likewise, new off-shore drilling in the Gulf of Mexico has, at least for the present, come to a standstill in the wake of the April 2010 BP/Deepwater Horizon oil spill.

The rippling effect of high crude oil prices on national economies is profound. Not only are gasoline and diesel the principal transportation fuels worldwide, crude petroleum also yields a vast array of chemicals that are feedstocks for an equally vast array of products, from plastics to pesticides. Thus, high crude oil prices spur worldwide price inflation as producers pass on their increased costs of production to consumers.

The economic difficulties caused by increasing demand coupled with diminishing supply is driving efforts to develop alternative and sustainable ways to meet energy and raw material needs. *The Roadmap for Biomass Technologies in the United States* (U.S. Department of Energy, Accession No. ADA436527, December 2002), authored by 26 leading experts, has predicted a gradual shift from a petroleum-based economy to a more carbohydrate dependent economy. This official document predicts that by 2030, 20% of transportation fuel and 25% of chemicals consumed in the United States will be produced from biomass. Such a shift away from petroleum-based technologies requires developing innovative, low-cost separation and depolymerization processing technologies to break down the highly oxygen-functionalized, polysaccharide molecules found in raw biomass to yield useful bio-derived materials and fuels. In short, abundant biomass resources can provide alternative routes for a sustainable supply of both transportation fuels and valuable intermediates (e.g., alcohols, aldehydes, ketones, carboxylic acid, esters) for production of drugs and polymeric materials. However, unless these alternative routes can be implemented at a production cost roughly comparable to the corresponding production cost when using petroleum feedstocks, the transition will inevitably be accompanied by severe economic dislocations. It is not enough that the transition can be accomplished; to avoid economic upheaval, the transition must be accomplished in an economically feasible fashion.

Furan derivatives (such as hydroxymethylfurfural (HMF), furfural (Fur) and furfuryl alcohol (FurA)) derived from renewable biomass resources have potential as substitutes for petroleum-based building blocks used to produce transportation fuels, plastics, and fine chemicals. For example, levulinic acid (LA) and levulinic acid esters can be produced directly from HMF (Girisuta et al., *Green Chemistry* 2006, 8, 701-709) and/or indirectly from furfural, via previous hydrogenation of furfural (Sitthisa et al. *J. Cat.* 277, 2011, 1-13, Merlo et al. *Catalysis Communications* 10, 2009, 1665-1669) to furfuryl alcohol (Lange et al. *Chemsuschem* 2009, 2, 437-441; Zhang et al. *Chemsuschem* 2011, 4, 112-118). LA is a valuable "platform" chemical for fabricating a host of downstream compounds. Furfural is also a key chemical for the commercial production of furan (via catalytic decarbonylation) and tetrahydrofuran (via hydrogenation), thereby providing a biomass-based alternative to the corresponding petrochemical production route (via dehydration of 1,4-butanediol). HMF can be used to produce 5-hydroxymethylfuranoic acid by oxidation of the formyl group or 2,5 dimethylfuran by hydrogenolysis.

Furfural is primarily used in refining lubricating oil. Furfural is also used in condensation reactions with formaldehyde, phenol, acetone or urea to yield resins with excellent thermosetting properties and extreme physical strength. Methyl-tetrahydrofuran (MeTHF), a hydrogenated form of furfural, is a principal component in P-series fuel, which is developed primarily from renewable resources. ("P-series fuel" is an official designation promulgated by the U.S. Dept. of Energy for a fuel blend comprised of pentanes, ethanol, and biomass-derived MeTHF. See 10 CFR §490.) Producing furfural from biomass requires raw materials rich in pentosan, such as corncobs, oat hulls, bagasse, and certain woods (like beech). Even today, most furfural production plants employ batch processing using the original, acid-catalyzed Quaker Oats technology. This technology was first implemented in 1921 by Quaker Oats in Cedar Rapids, Iowa as a means to realize value from the tons of oat hulls remaining after making rolled oats. For an exhaustive history on the production of furfural, see K. J. Zeitsch, "The Chemistry and Technology of Furfural and its Many By-Products," Elsevier, Sugar Series, No. 13, © 2000, Elsevier Science B.V.) This batch processing results in yields less than 50%, and also requires a large amount of high-pressure steam. The process also generates a significant amount of waste.

Various researchers have tried dehydration of xylose into furfural using acid catalysts such as mineral acids, zeolites, acid-functionalized Mobile crystalline materials (MCM's) and heteropolyacids. Moreau et al. has conducted the reaction in a batch mode using H-form faujasites and a H-mordenite catalyst, at 170° C., in a solvent mixture of water and methylisobutylketone (MIBK) or toluene (1:3 by vol) with selectivities ranging from 70-96% (in toluene) and 50-60% (in MIBK) but at low conversions. Dias et al. showed that a sulfonic acid-modified MCM-41-type catalyst displayed fairly high selectivity to furfural (~82%) at high xylose conversion (>90%) with toluene as the extracting solvent for the reactions carried out 140° C. In the patent literature, see, for example, U.S. Pat. Nos. 4,533,743 (to Medeiros et al.); 4,912, 237 (to Zeitsch); 4,971,657 (to Avignon et al.); and 6,743,928 (to Zeitsch).

5-hydroxymethylfurfural (HMF) is of interest as a lignocellulose ($C_6$-derived) platform chemical which offers multiple upgrading strategies to various intermediates, polymer feedstocks, specialty chemicals, and transportation fuels. Progress in HMF production via sugar (generally glucose or fructose) dehydration has been compiled in several reviews. See M. S. Feather, J. F. Harris, R. S. T. a. D. Horton, Dehydration Reactions of Carbohydrates, in: Advances in Carbohydrate Chemistry and Biochemistry, Academic Press, 1973, pp. 161-224; B. F. M. Kuster, Starch-Starke, 42 (1990) 314-321; J. Lewkowski, *Arkivoc*, 2 (2001); and X. Tong, Y. Ma, Y. Li, *Applied Catalysis A: General*, 385, 1-13.)

Multiple systems for fructose dehydration have been proposed, and these systems are conceptually extensible to glucose sugars, which may be isolated from cellulose. Alternatively, glucose produced through cellulose hydrolysis may undergo isomerization via acid-, base-, or enzyme-catalyzed reactions to yield fructose, which may be processed in any of the following systems. The simplest is dehydration of fructose in aqueous media using either solid or homogeneous mineral acid catalysts. Unfortunately, HMF is sufficiently reactive under such conditions such that it undergoes rehydration to form levulinic and formic acids. (B. F. M. Kuster, H. M. G. Temmink, Carbohydrate Research, 54 (1977) 185-191.) Additionally, HMF may undergo condensation reactions either with itself or other polyoxygenates to form insoluble humins, limiting HMF yields. (B. Girisuta, L. P. B. M. Janssen, H. J. Heeres, Green Chemistry, 8 (2006) 701-709. B. Girisuta, L. Janssen, H. J. Heeres, *Industrial & Engineering Chemistry Research*, 46 (2007) 1696-1708.) The problem of levulinic acid formation may be alleviated by processing fructose in non-aqueous solvents, wherein rehydration of HMF to form levulinic acid is less likely. Of the multiple non-aqueous solvents considered (A. Corma, S. Iborra, A. Velty, Chemical Reviews, 107 (2007) 2411-2502.), DMSO has shown the most promise, with HMF yields in excess of 90% achieved using acidic resins. A disadvantage of non-aqueous processing is the low solubility of sugars in organic solvents, which limits sugar loading and thus the large-scale applicability of the technology.

Biphasic reactors for fructose dehydration have been exploited for a number of years, and both homogeneous and heterogeneous acid catalysts have demonstrated promise. For example, Moreau and co-workers demonstrated that biphasic water-MIBK systems coupled with zeolites (i.e., mordenite) of varying Si/Al ratios could achieve high HMF selectivities (>90%), at moderately high conversions (76%) of fructose (C. Moreau, R. Durand, S. Razigade, J. Duharnet, P. Faugeras, P. Rivalier, P. Ros, G. Avignon, *Applied Catalysis A: General*, 145 (1996) 211-224). Such systems, however, are limited by a sparse partitioning of HMF into the organic phase (MIBK) which restricts HMF concentration in the extracting solvent and necessitates large quantities of solvent Abundant biomass resources are a promising sustainable supply of valuable intermediates (e.g., alcohols, aldehydes, ketones, carboxylic acids) to the chemical industry for producing drugs and polymeric materials. In this context, the high content of oxygenated functional groups in carbohydrates, the dominant compounds in biomass, is an advantage. This is in contrast to the drawbacks of such functionality for the conversion of carbohydrates to fuels. However, there remains a long-felt and unmet need for efficient processes to selectively remove excess functional groups and to modify other functional groups to create commercially desirable products from biomass.

SUMMARY OF THE INVENTION

The present invention is a method for the selective dehydration of $C_5$ and $C_6$ carbohydrates (preferably xylose, fructose and glucose) to produce furfural and hydroxymethylfurfural and other furan derivatives, such as furfuryl alcohol, levulinic acid, levulinate esters, and/or gamma-valerolactone using alkylphenols as a solvent. The alkylphenol centered processing strategy outlined herein is advantageous because it provides a cost-effective route for making these valuable chemical intermediates from biomass.

Disclosed is a process to make furanic products (HMF, furfural) and any of their derivatives (furfuryl alcohol, LA, levulinate esters, GVL). In one version, the process entails dehydrating a feedstock solution containing a carbohydrate, in the presence of an acid catalyst, in a biphasic reaction vessel containing an aqueous reaction solution, an acid catalyst, and a substantially immiscible organic extraction solution comprising at least one alkylphenol. The furan derivatives formed in the aqueous reaction solution are continuously extracted into the organic extracting solvent, minimizing size reactions, such as polymerization to form humins. Primary products, such as furfural and hydroxymethylfurfural can be isolated if desired. Alternatively, they may be processed with or without isolation from the alkylphenol solvent to obtain other derivatives such as furfuryl alcohol, levulinic acid, levulinate esters, and/or GVL. The lack of purification reduces the production cost for these derivative compounds, which have a high production cost in traditional strategies for furan production and processing.

Preferably, the aqueous solution described herein comprises a mineral, organic or solid acid, such as hydrochloric acid, nitric acid, phosphoric acid, sulfuric acid, boric acid, hydrofluoric acid, hydrobromic acid, acetic acid, oxalic acid, sulfonic acid, trifluoroacetic acid, sulfated zirconia, zeolites, ion exchange resins and/or heteropolyacids, or high temperature water.

A version of this process can be used to form furfural (from $C_5$ sugars), which may be isolated from the alkylphenol extracting solvent through conventional separation strategies as a final product. Alternatively, the furfural so formed in biphasic dehydration may be hydrogenated, with or without separation from the alkylphenol extracting solvent, to yield furfuryl alcohol, which may be either recovered as a final product or further processed (with or without purification) to give products, such as levulinic acid, levulinate esters, or γ-valerolactone, for which processes are outlined herein.

For example, in another version of the process, furfuryl alcohol may be converted into levulinic acid (through contact with an aqueous solution preferentially containing an acidic catalyst) or levulinate esters (through contact with an esterifying solvent such as alcohols or olefins). Either upgrading strategy may occur in mono- or biphasic systems. See, for example, Lange et al., U.S. Pat. No. 7,265,239, for a single-phase reaction. In the present method a two-phase reaction system is preferred so that furfuryl alcohol is released slowly to the aqueous phase as it is converted into LA/LA esters. In this fashion, the furfuryl alcohol concentration in the water phase is always low (which minimizes unwanted side reactions). (See FIG. 2B, which illustrates a biphasic approach.) The levulinic acid or levulinate ester products may be recovered in high yield as a final product. Alternatively, they may undergo further processing to a number of intermediates in strategies which generally do not require isolation from the organic solvents in which they are prepared.

In another version, which preferentially focuses on $C_6$ sugars found in biomass, biphasic reactors utilizing AP extracting solvents can be used to form hydroxymethylfurfural (produced through dehydration of $C_6$ sugars), which may be isolated or purified as the final product. Alternatively, HMF, with or without isolation from the alkylphenol extracting solvent, can be converted into levulinic acid and formic acid by contact with an aqueous solution preferentially containing an acid catalyst in a second biphasic system. In the presence of alcohols and/or olefins, esters of levulinic and formic acid will be formed. Once formed, levulinic and formic acids and esters are continuously extracted into the organic phase comprising at least one alkylphenol. The levulinic and formic acids and esters may be isolated or purified as the final product of the method. Alternatively, they may undergo further processing to a number of products (such as GVL) with or without isolation from the alkylphenol extracting solvent.

In another version of the process, levulinic acid and/or levulinate esters so produced through any of the above described scenarios from either $C_5$ or $C_6$ sugars may be reduced with or without isolation from extracting solvents to yield γ-valerolactone. The γ-valerolactone product may be thus formed in an organic extracting solvent comprising at least one alkylphenol.

Another version of the method is directed to making levulinic acid by dehydrating a feedstock solution comprising a carbohydrate in an aqueous reaction solution, in the presence of an acid catalyst, to yield furfural. The aqueous reaction is extracted with a substantially immiscible organic extraction solution comprising at least one alkylphenol, wherein furfural is extracted into the organic extraction solution. The furfural is hydrogenated into furfuryl alcohol. The furfuryl alcohol is then converted into levulinic acid or a levulinate ester in the presence of an alkylphenol.

Similarly, another version of the method is directed to a method of making levulinic acid by dehydrating a feedstock solution comprising a carbohydrate in an aqueous reaction solution, in the presence of an acid catalyst, to yield hydroxymethylfurfural (HMF). The aqueous reaction solution is extracted with a substantially immiscible organic extraction solution comprising at least one alkylphenol, wherein HMF is extracted into the organic extraction solution. The HMF is converted into levulinic acid or a levulinic acid ester. The levulinic acid or levulinic acid ester is extracted into an organic extraction solution comprising at least one alkylphenol.

The method can also be implemented to yield HMF as the furan derivative. The HMF itself is a valuable chemical and can isolated or purified as the final product. Alternatively, the HMF can be converted into an HMF (which also may optionally be isolated or purified if desired). The HMF-ethers may alternatively be converted into levulinic acid or levulinate ester, which may optionally be isolated or purified and/or converted into GVL.

As representative end products of the process partition into an organic phase containing an alkylphenol at the process conditions described herein, all or a portion of the final products (for example, but not limited to, furfural, HMF, levulinic acid, levulinate esters, or γ-valerolactone in the solvent) may be recycled for further use as an extracting phase. This serves to increase the final attainable concentration of the desired product (for example but not limited to, furfural, HMF, levulinic acid, levulinate esters, or γ-valerolactone in an extracting solvent), which facilitates a less energy demanding recovery of said products, by distillation as an example.

In all versions of the method, the organic extraction solvent preferably comprises at least one alkylphenol selected from the group consisting of:

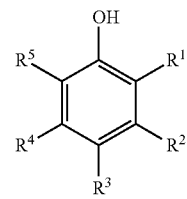

wherein $R^1$-$R^5$ are independently selected from the group consisting of hydrogen, hydroxyl, and $C_1$-$C_{24}$ linear, branched, or cyclic alkyl, provided that at least one of $R^1$-$R^5$ is alkyl. All positional isomers (ortho, meta, para) are explicitly included, as are compounds having more than one hydroxy group, e.g., alkyl-substituted-1,4-dihydroxybenzene. Mono- and di-alkylphenols are preferred, as are APs wherein the alkyl substituent(s) is a $C_1$-$C_{12}$ linear, branched, or cyclic alkyl, more preferably still a $C_1$ to $C_6$ linear or branched alkyl.

Several strategies are outlined herein that facilitate selective hydrogenation of targeted functional groups in the presence of an alkylphenol solvent. In this manner, chemical conversion may be achieved without purification of intermediate compounds, offering a significant advantage over the state of the current state of the art. In particular, the hydrogenation strategies described herein facilitate the selective reduction of carbonyl groups (C=O) as opposed to other chemical functionalities. The selective hydrogenations described herein can be accomplished in several ways. The hydrogenation may occur in the presence of a catalyst comprising one or more metals either supported or unsupported from Groups 6-14 of the periodic table, more preferably still a catalyst comprising ruthenium, nickel, platinum, palladium, rhodium, tin, copper, chromium and combinations thereof, and most preferably a catalyst comprising ruthenium and tin for hydrogenation of LA, ruthenium for the hydrogenation of LA esters and platinum and tin for the hydrogenation of furfural. Such materials have demonstrated appropriate selectivity to allow direct processing of unrefined intermediates without their isolation from extracting solvents.

Alternatively, any requisite hydrogenation described herein may also be accomplished by hydrogen transfer using homogeneous or solid oxide catalysts in the presence of a hydrogen donor, such as an alcohol. In transfer hydrogenation of levulinic acid, production rates and catalyst stability can be improved by first converting the LA into a LA ester (by acid-catalyzed reaction with an alcohol or an olefin) and then reducing the LA ester to GVL and the corresponding alcohol by transfer hydrogenation. Preferably, the LA ester is reduced to GVL in the presence of a solid oxide catalyst. Transfer hydrogenation offers comparable selectivity to strategies using molecular hydrogen and may thus be used for upgrading furans and their derivatives (furfural, LA) without requiring their isolation from extracting solvents used in their preparation or recovery and offers a low-cost, hydrogenation avenue which does not require traditional precious metal catalysts.

The overall strategy described herein is to convert lignocellulosic biomass to value-added fuels and chemicals by partially removing oxygen to yield reactive intermediates (denoted herein as platform molecules, such as HMF, fur, furA, LA, LA esters, GVL, and others). The platform molecules are valuable and useful commercial products. The platform molecules can be converted into any number of desired final products, including liquid transportation fuels. As a general proposition, platform molecules have fewer functional groups as compared to the carbohydrates found naturally in biomass (e.g., xylose, glucose). Because there are fewer reactive functional groups, the platform molecules can be selective upgraded to other useful chemicals via catalytic upgrading processes.

For example, a variety of fuels and chemicals can be made from LA (3, 4), such as valeric acid esters (5), methyltetrahydrofuran (6-8), esters and ketals of LA (9), γ-valerolactone (GVL) (10, 11), which can be used directly as a fuel additive (12), or as a precursor for fuels (13) and chemicals (14, 15). While the furans can be formed in significant yields (50-90%) by cellulose/hemicellulose deconstruction in aqueous solutions of mineral acids such as sulfuric acid (SA) (16, 17), a challenge for profitable, large-scale production of these furan derivatives has been separating them from the mineral acid used in the process. In traditional processing schemes, purification is necessary so that intermediates may be further upgraded in downstream stages without negative effects of residual impurities such as mineral acids used in biomass deconstruction and/or sugar dehydration (18). In the present method, alkylphenol (AP) solvents (19) are used as a partitioning agents in multiple methods which provide pathways for the production of HMF, fur, furA, LA and/or GVL from biomass in general, and lignocellulosic biomass in particular.

FIG. 1A provides a conceptual example of the technology which generalizes readily to the multiple strategies described in detail below. In this example, xylose sugars present in a reactive aqueous phase (preferentially containing an acid catalyst) undergo dehydration to form furfural. Furfural partitions very favorably into alkylphenols and is continuously extracted into the organic phase upon formation. This serves to minimize its concentration in the reactive aqueous phase which decreases the incidence of side reactions and maximizes furfural yields. In the strategies disclosed herein, the use of alkylphenols as an extracting phase gives rise to multiple significant advantages over the current state of the art. In general, these are related to its broad capabilities as an extracting phase which favorably partitions multiple biomass-derived intermediates.

Further, alkylphenols are sufficiently non-reactive to allow catalytic conversion of intermediates without purification. For example, because AP solvents have favorable partition coefficients for desired intermediates, the method requires only a single-stage extraction for product recovery. Additionally, AP solvents do not extract water or acids present therein. As such, acidic solutions used to deconstruct carbohydrates (cellulose/hemicellulose) may be recycled without complex purification, allowing sustainable recovery of both water and the acid catalyst for further biomass deconstruction. Moreover, the water present in the cellulose/hemicellulose deconstruction need not be separated from reaction products by evaporation at any stage, offering reduced energy demands in the strategies proposed herein. Further, because representative end products of this process partition into a non-reactive organic phase or are otherwise inert at the process conditions described herein, all or a portion of the final products (for example but not limited to, furfural, HMF, or γ-valerolactone in an extracting solvent) may be recycled for further use as an extracting phase. This serves to increase the final attainable concentration of the desired product (for example but not limited to, furfural, HMF, or gamma-valerolactone in an extracting solvent), which facilitates a less energy demanding recovery of said products, by distillation as an example. Ultimately, separation strategies (such as distillation) may be used to recover desired products (GVL, for example) from AP solvents. In these instances, all of the products of interest have lower boiling points than the AP solvent and thus can be recovered at a high purity via simple distillation without requiring solvent evaporation.

Other advantages arise from the low-reactivity of alkylphenol solvents, in particular during selective hydrogenation strategies described herein. Intermediates may be upgraded without recovery from the extracting phase, offering simple processing strategies with reduced energy and equipment demands. In addition, many of the unique properties of biphasic systems formed by combining AP extracting solvents with aqueous phases offer novel strategies for the selective processing of reactive intermediates such as furfural, HMF, or furfuryl alcohol, which are difficult to process in conventional strategies because of their high reactivity.

As a final advantage, the strategies outlined herein offer an integrated method by which all of the carbohydrate content of biomass (specifically, $C_5$ and $C_6$ sugars) may be converted into furanic intermediates (HMF, furfural, etc.) or any of their derivatives (furfuryl alcohol, LA, GVL). Thus, the use of alkylphenol extracting solvents provides a concerted process design by which all of the sugar content in biomass may be converted selectively to common platform molecules which are of broad interest in biorefining, such as levulinic acid or GVL.

DETAILED DESCRIPTION

Abbreviations and Definitions

Figure 1A:
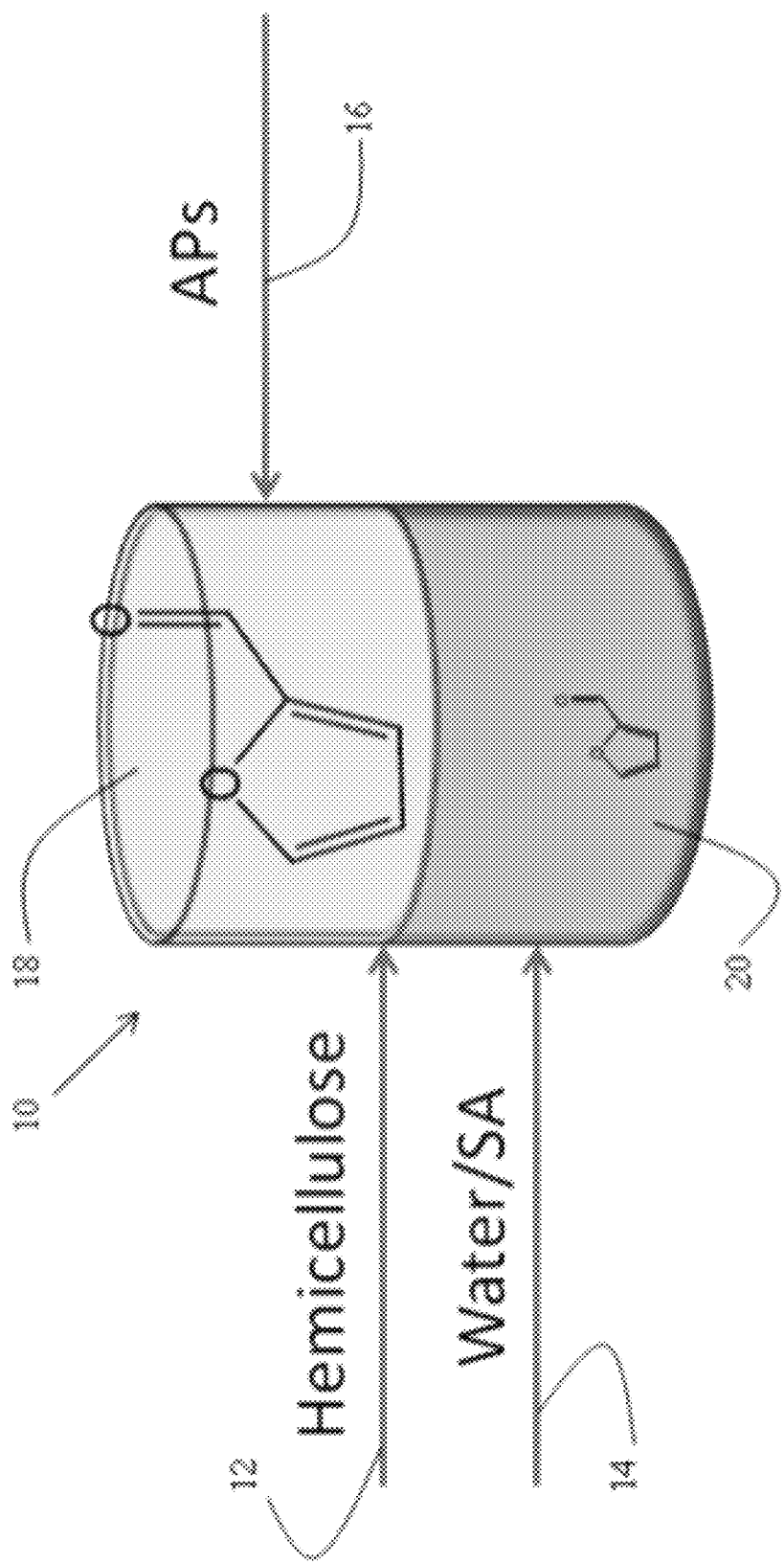
FIG. 1A is a schematic diagram depicting the acid-catalyzed production of furfural from hemicellulose or C5 sugars derived from hemicellulose in a biphasic reaction in which the lower layer 20 is aqueous and the upper layer 18 is organic and comprises one or more alkylphenols (APs).

AP=alkylphenol. As used herein, an alkylphenol is defined as a compound having the formula:

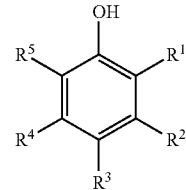

wherein $R^1$-$R^5$ are independently selected from the group consisting of hydrogen, hydroxyl, esters, ethers, carboxylic acids, and $C_1$-$C_{24}$ linear, branched, or cyclic alkyl or alkene, provided that at least one of $R^1$-$R^5$ is alkyl. All positional isomers (ortho, meta, para) are explicitly included, as are compounds having more than one hydroxy group, e.g., alkyl-substituted-1,4-dihydroxybenzene. Mono- and di-alkylphenols are preferred, as are APs wherein the alkyl substituent(s) is a $C_1$-$C_{12}$ linear, branched, or cyclic alkyl, more preferably still a $C_1$ to $C_6$ linear or branched alkyl.

BL=butyl levinulate.

"Biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. "Biomass" includes virgin biomass and/or non-virgin biomass such as agricultural biomass, commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like.

FA=formic acid. FID=flame ionization detector. GVL=γ-valerolactone. HPLC=high-performance liquid chromatography.

As used herein, the term "hydrogenation catalyst" refers without limitation to any catalyst, now known or developed in the future, homogenous or heterogeneous, that catalyzes the hydrogenation of carbonyl bonds (C═O). Preferred catalysts will reduce carbonyl bonds preferentially as opposed to reducing carbon-carbon double bonds (C═C). The activities need not be exclusive, but the chosen catalyst should catalyze the hydrogenation of C═O bonds at a rate much faster than it catalyzes the hydrogenation of C═C bonds. Catalysts comprising one or more metals from Groups 6-14 are preferred, also these metals doped with gallium, boron, germanium, indium and/or tin. Ruthenium, nickel, platinum, copper, chromium and rhodium (alone, in combination, alloyed with other metals, and/or doped with gallium, germanium, indium and/or tin) are preferred. Other hydrogenation catalysts may also be used, such as metal hydrides (e.g., $NaBH_4$), polyoxometalates, Raney Ni, Raney Cu, etc. The catalysts may be used with or without a support, where any carbon, polymer, or solid oxide may comprise "support."

Selective reduction may also be accomplished by transfer hydrogenation using a hydrogen donor. The term "hydrogen donor" refers to any compound with the ability to transfer an equivalent of molecular hydrogen to a second compound. Exemplary hydrogen donors include, but are not limited to alcohols, polyols, olefins, cycloalkenes, carboxylic acids, and esters.

The rate of hydrogen transfer can be increased by using homogeneous or heterogeneous catalysts. Exemplary catalysts include, but are not limited to, metals, zeolites, metal oxides supported or unsupported such as MgO, $ZrO_2$, gamma-$Al_2O_3$, $CeO_2$, $CeZrO_x$, $MgOAl_2O_3$, $Mg/Al/ZrO_x$, $MgO/SiO_2$, $CeO_2$—ZnO, Sn-beta-zeolite, Ti-beta-zeolite, Sn-containing mesoporous silica, as well as metal salts and complexes of Pd, Pt, Ru, Ir, Rh, Fe, Ni, Co, Os, Mo. A full list of suitable hydrogen donors and catalysts can be found in R. A. W Johnsotne & A. H Wilby (1985) "Heterogeneous catalytic transfer hydrogenation and its relation to other methods for reduction of organic compounds," *Chem. Rev.* 85: 129-170, which is incorporated herein by reference.

IPA=isopropyl alcohol. LA=levulinic acid. Mineral acid=any mineral-containing acid, including (by way of example and not limitation), hydrochloric acid, nitric acid, phosphoric acid, sulfuric acid, boric acid, hydrofluoric acid, hydrobromic acid, and the like). MTHF=methyltetrahydrofuran. Organic acid=any organic acid, without limitation, such as toluensulfonic acid, formic acid, acetic acid, oxalic acid, trifluoroacetic acid, and the like. SA=sulfuric acid. SBP=sec-butyl phenol.

A "separator" is any device now known or developed in the future which is dimensioned and configured to substantially separate or enrich two or more liquids from one another. Explicitly included within the word "separator" are distillation columns of any and all description, including batch and continuous distillation columns, in any format, e.g., simple, fractional, steam, vacuum, and short-path distillation columns.

A "solid acid catalyst" can comprise one or more solid acid materials. The solid acid catalyst can be used independently or alternatively can be utilized in combination with one or more mineral acid or other types of catalysts. Exemplary solid acid catalysts include, but are not limited to, heteropoly acids, acid resin-type catalysts, meso-porous silicas, acid clays, sulfated zirconia, molecular sieve materials, zeolites, and acidic material on a thermo-stable support. Where an acidic material is provided on a thermo-stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.) which may optionally be doped with additional acid groups such as $SO_4$ may also be used as solid acid catalysts.

Further examples of solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. The functional group is generally of the sulfonic acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

TCD=thermal conductivity detector. WHSV=weight hour space velocity. XRD=X-ray diffraction.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of methods or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry.

Biomass to Fufural, hydroxymethylfurfural, Furfuryl Alcohol, Levulinic Acid, Gamma-Valerolactone, and the Like:

A first version of the method, a simple route to yield furfural from biomass, is schematically depicted in FIG. 1A. Here, a biomass feedstock 12, such as lignocellulose, cellulose, hemicelluloses, sugars, etc. is introduced into a reaction vessel 10 containing an acidic aqueous solution 20. The solution is preferably acidified with a mineral acid, but any strong acid will do, so long as it degrades/deconstructs the carbohydrates found in the feedstock 12 to yield furfural. The digested, aqueous, acidic solution containing furfural is continuously extracted into a second, organic phase 18 containing one or more alkylphenols (AP, 16). The AP is not soluble with the aqueous reaction solution 20, so the extraction yields a biphasic system—an upper organic layer 18 (containing AP and furfural) and a lower aqueous layer containing the acid (sulfuric acid, SA, as an exemplary embodiment in FIG. 1A) and unreacted biomass (principally lignin and unconverted cellulose). The furfural partitions preferentially into the AP, while the acid, lignin and any un-reacted cellulose remain in the aqueous phase. The furfural so formed can be separated from the AP by any means now known or developed in the future, such as by distillation (not shown in FIG. 1A). (A separator 32 is depicted in FIGS. 3-7 and may be any device now known or developed in the future which is dimensioned and configured to substantially separate or enrich two or more liquids from one another. Explicitly included within the word "separator" are distillation columns of any and all description, including batch and continuous distillation columns, in any format, e.g., simple, fractional, steam, vacuum, and short-path distillation columns.)

As noted in the definitions, the preferred APs for use in the method include one or two alkyl groups that are linear or branched, and generally have six or fewer carbon atoms. (Note that these are just the preferred APs; other may be used and are explicitly within the scope of the method.) APs preferentially extract furfural, furfuryl alcohol, LA, and GVL from aqueous acidic solutions, with representative partition coefficients given in Table 1.

In this method, the final concentration of furfural in the alkylphenol can be increased by recycling the furfural/AP organic phase produced from a single charge of biomass serve as an extracting phase for subsequent cycles of furan production. Additionally, yields to furfural in a single stage can be increased by saturating the aqueous acidic phase with salts, such as NaCl which improves the partitioning of furfural into the extracting solvent.

Figure 1B:
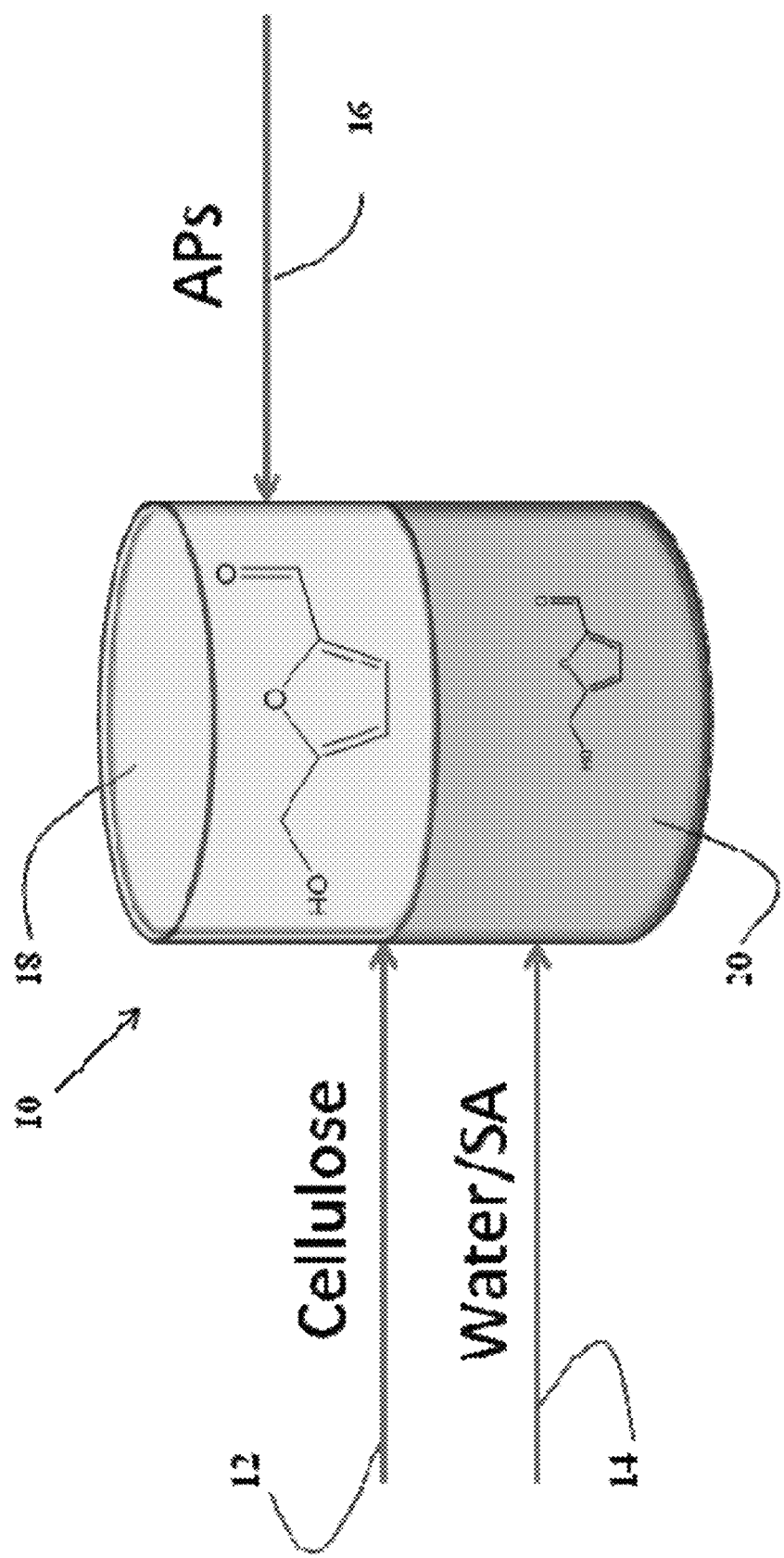
FIG. 1B is a schematic diagram depicting the acid-catalyzed production of hydroxymethylfurfural from cellulose, hemicellulose, or C6 sugars derived from either in a biphasic reaction in which the lower layer 20 is aqueous and the upper layer 18 is organic and comprises one or more alkylphenols (APs).

Alongside furfural, this method may also be used to produce hydroxymethylfurfural, as schematically depicted in FIG. 1B. Here, a biomass feedstock 12, such as lignocellulose, cellulose, hemicelluloses, sugars, etc. is introduced into a reaction vessel 10 containing an aqueous solution 20. The solution is preferably acidified with a mineral acid, but any strong acid will do, so long as it degrades/deconstructs the carbohydrates found in the feedstock 12 to yield hydroxymethylfurfural. The digested, aqueous, acidic solution containing hydroxymethylfurfural is continuously extracted into a second, organic phase (18) containing one or more alkylphenols (AP, 16). The AP is not soluble with the aqueous reaction solution 20, so the extraction yields a biphasic system—an upper organic layer 18 (containing AP and hydroxymethylfurfural) and a lower aqueous layer containing the acid (sulfuric acid, SA, as an exemplary embodiment in FIG. 1B) and unreacted biomass (principally lignin). The hydroxymethylfurfural partitions preferentially into the AP, while the acid, lignin and any un-reacted cellulose remain in the aqueous phase. The hydroxymethylfurfural so formed can be separated from the AP by any means now known or developed in the future, such as by distillation (not shown in FIG. 1B). A separator 32 is depicted in FIGS. 3-7 and may be any device now known or developed in the future which is dimensioned and configured to substantially separate or enrich two or more liquids from one another. Explicitly included within the word "separator" are distillation columns of any and all description, including batch and continuous distillation columns, in any format, e.g., simple, fractional, steam, vacuum, and short-path distillation columns.

In this method, the final concentration of HMF in the alkylphenol can be increased by recycling the HMF/AP organic phase produced from a single charge of biomass, serving as an extracting phase for subsequent cycles of furan production. Additionally, yields to HMF in a single stage can be increased by saturating the aqueous acidic phase with salts, such as NaCl which improves the partitioning of HMF into the extracting solvent.

Figure 2A:
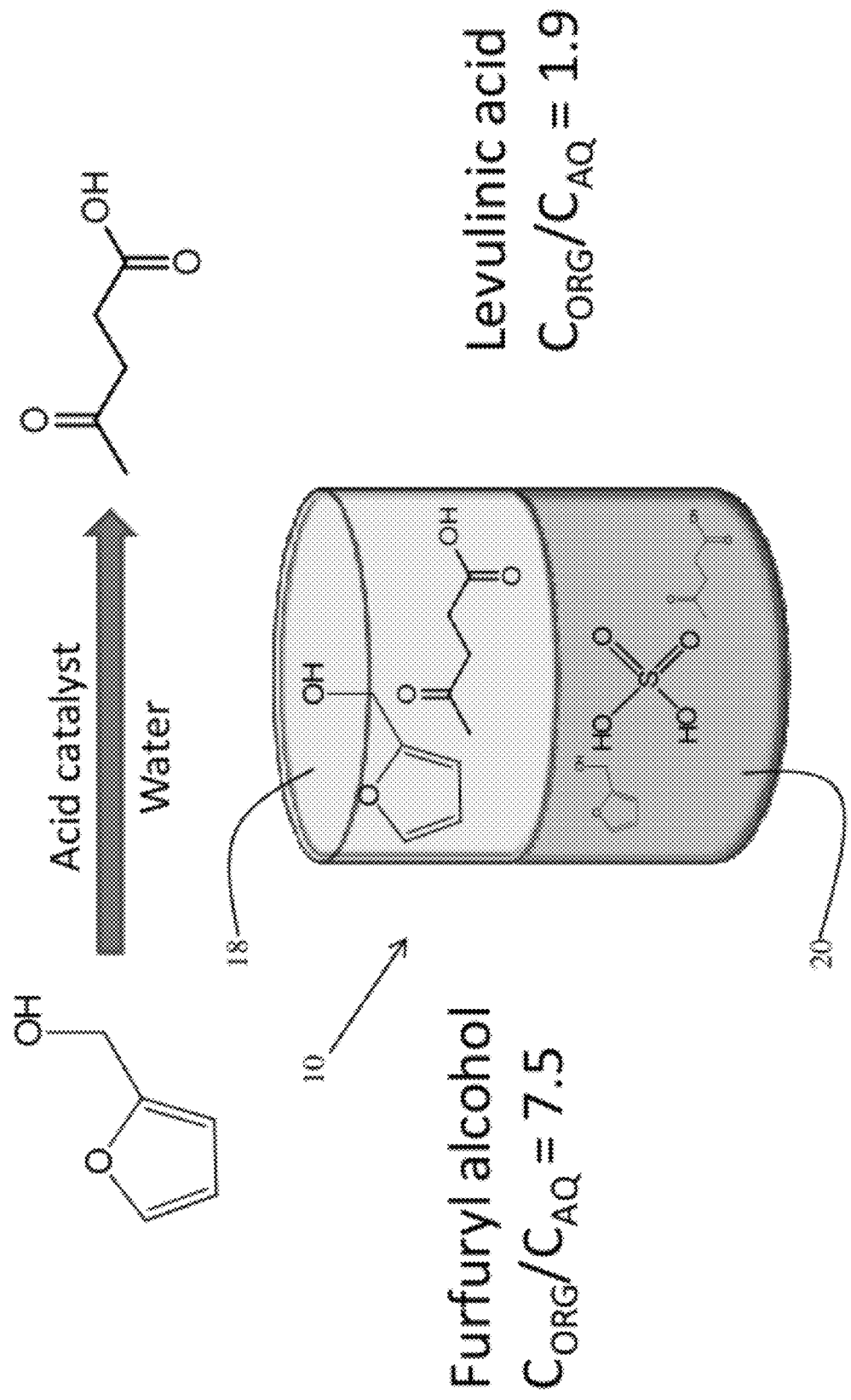
FIG. 2A is a schematic diagram depicting the reaction to convert furfuryl alcohol into levulinic acid in a biphasic system containing a reactive, aqueous acidic layer 20 an extracting solvent 18 comprising at least one alkylphenol.

FIG. 2A is a schematic illustration of another version of the method in which a biphasic system (10) containing a reactive aqueous phase (20) and a non-reactive, organic extracting phase containing at least one alkylphenol solvent (18) may be used to convert furfuryl alcohol into levulinic acid. Leveraging previously described strategies, furfuryl alcohol may be produced by hydrogenation of furfural formed through dehydration of $C_5$ sugars in biomass resources. In this method, highly reactive furfuryl alcohol is favorably partitioned into inert organic phase 18 and minimally partitioned into the reactive aqueous phase (20). The presence of the AP phase simulates a semi-batch reactor as furfuryl alcohol is released from the organic to the aqueous phase slowly as the furfuryl alcohol present in the catalytic aqueous phase is converted into LA, continuously maintaining low concentrations of furfuryl alcohol in the aqueous phase, leading to high yields of levulinic acid due to a decreased incidence of furfuryl alcohol degradation, which occurs at higher concentrations. As noted in FIG. 2A, furfuryl alcohol partitions into the organic phase 18 with a partition coefficient of 7.5. Upon completion of the reaction, the system shown in FIG. 2A contains an upper organic layer (18) (containing the AP solvent and any extracted furfuryl alcohol and LA) and a lower aqueous layer (20) containing any acid catalyst.

LA partition coefficients and boiling points for the most preferred APs are shown in Table 1 (The values were generated using a 50/50 wt % solution of the stated AP and water containing 2M LA, 2M formic acid, and $0.5H_2SO_4$.)

TABLE 1

| Structure | Partition Coeff. M/M (% of LA in org. phase) | AP Boiling Point (° C.) |
|---|---|---|
| OH with tert-butyl (ortho) | 2.66 (82%) | 224 |
| OH with sec-butyl (ortho) | 1.94 (78%) | 228 |
| OH with sec-butyl (para) | 1.15 (70%) | 245 |
| OH with $C_5H_{11}$ (para) | 1.1 (70%) | 265 |
| OH with $C_6H_{13}$ (para) | 0.8 (60%) | 280 |

TABLE 1-continued

| Structure | Partition Coeff. M/M (% of LA in org. phase) | AP Boiling Point (°C.) |
|---|---|---|
| OH–C6H4–$C_9H_{19}$ | 0.4 (40%) | 310 |
| OH–C6H4–$C_{12}H_{25}$ | 0.36 (30%) | 334 |

The % value in parenthesis is the amount of LA detected in the organic phase after the extraction. For comparison, the partition coefficients for HMF, furfural, and furfuryl alcohol in sec-butylphenol are approximately equal to 7, 25, and 7.5 respectively.

Figure 2B:
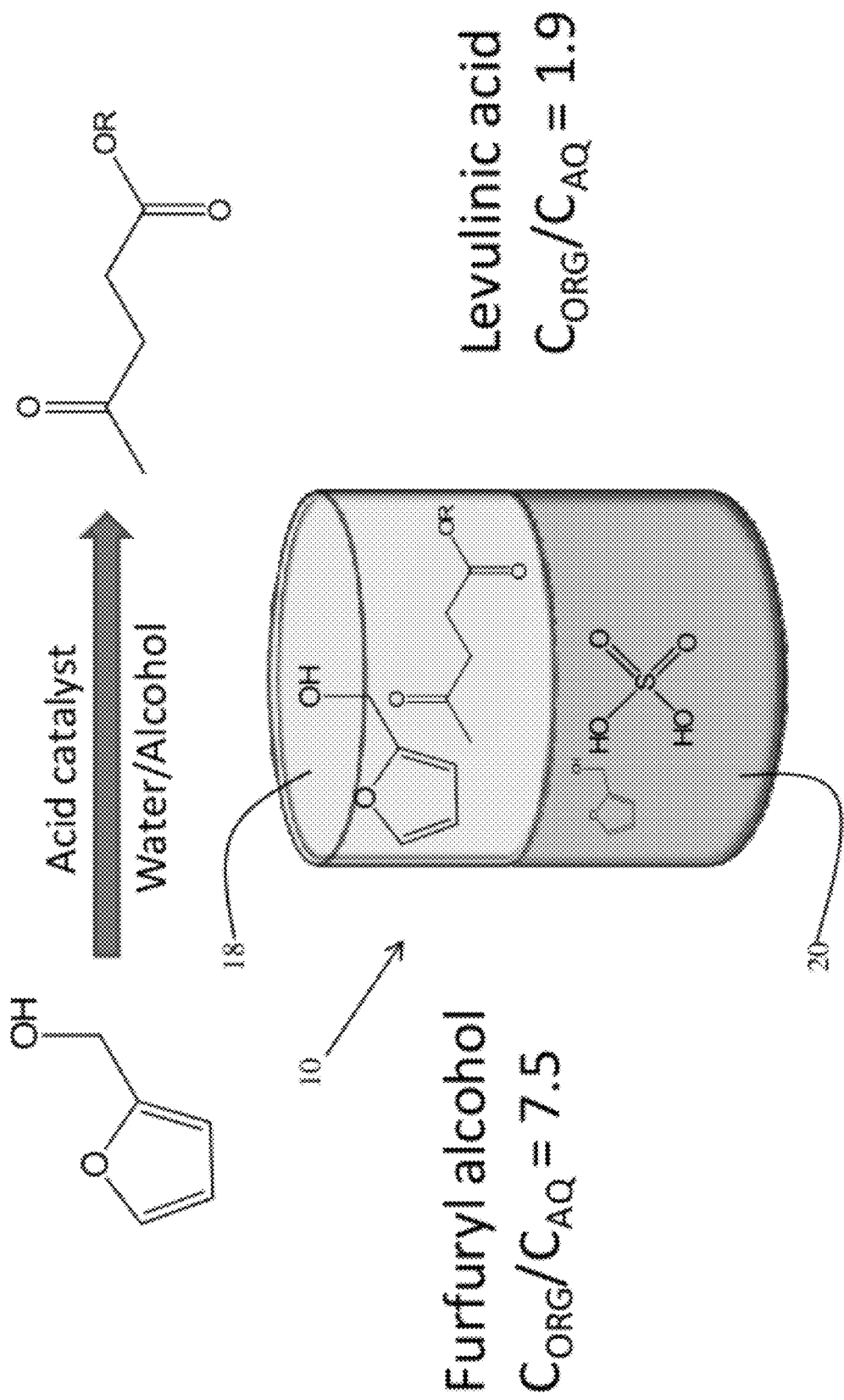
FIG. 2B is a schematic diagram depicting the reaction to convert furfuryl alcohol into levulinate esters in a biphasic system containing a reactive aqueous/alcohol acid reaction layer 20 and an extracting solvent 18 comprising an alkylphenol.

FIG. 2B is a schematic illustration of another version of the method in which furfuryl alcohol, formed by hydrogenation of the biphasic dehydration product furfural, as described previously, may be converted to levulinate esters as opposed to levulinic acid. This strategy relies upon the introduction of an esterifying reagent (such as an alcohol or an olefin) and an acidic catalyst to solutions of furfuryl alcohol in alkylphenols formed by selective hydrogenation of furfural in the extracting solvent. This strategy allows selective conversion of furfuryl alcohol to levulinate esters. Upon completion of the reaction, system 10 of FIG. 2B is preferably comprised of single phase containing the AP solvent (though biphasic systems are also appropriate), any unconverted furfuryl alcohol and any LA ester products. Typically, a solid acid catalyst would be used for this reaction and recovered spontaneously from the liquid reaction products. A biphasic system (as presented in the figure) can be alternatively formed by adding an aqueous layer to the solutions of furfuryl alcohol in alkylphenols formed by selective hydrogenation of furfural in the extracting solvent. In this case solid or homogeneous catalysts can be used. The presence of the AP phase simulates a semi-batch reactor where furfuryl alcohol is released from the organic to the aqueous phase slowly as the furfuryl alcohol present in the catalytic aqueous phase is converted into LA esters, maintaining low concentrations of furfuryl alcohol in the aqueous phase and leading to high yields of LA esters due to a decreased incidence of furfuryl alcohol degradation, which occurs at higher concentrations. The AP in organic phase 18 is not soluble with the aqueous acidic reaction solution 20, so the extraction yields a biphasic system—the upper organic layer in vessel 10 (containing AP and extracted furfural alcohol and LA ester) and a lower aqueous layer containing the acid, and other unreacted reactants.

Figure 3A:
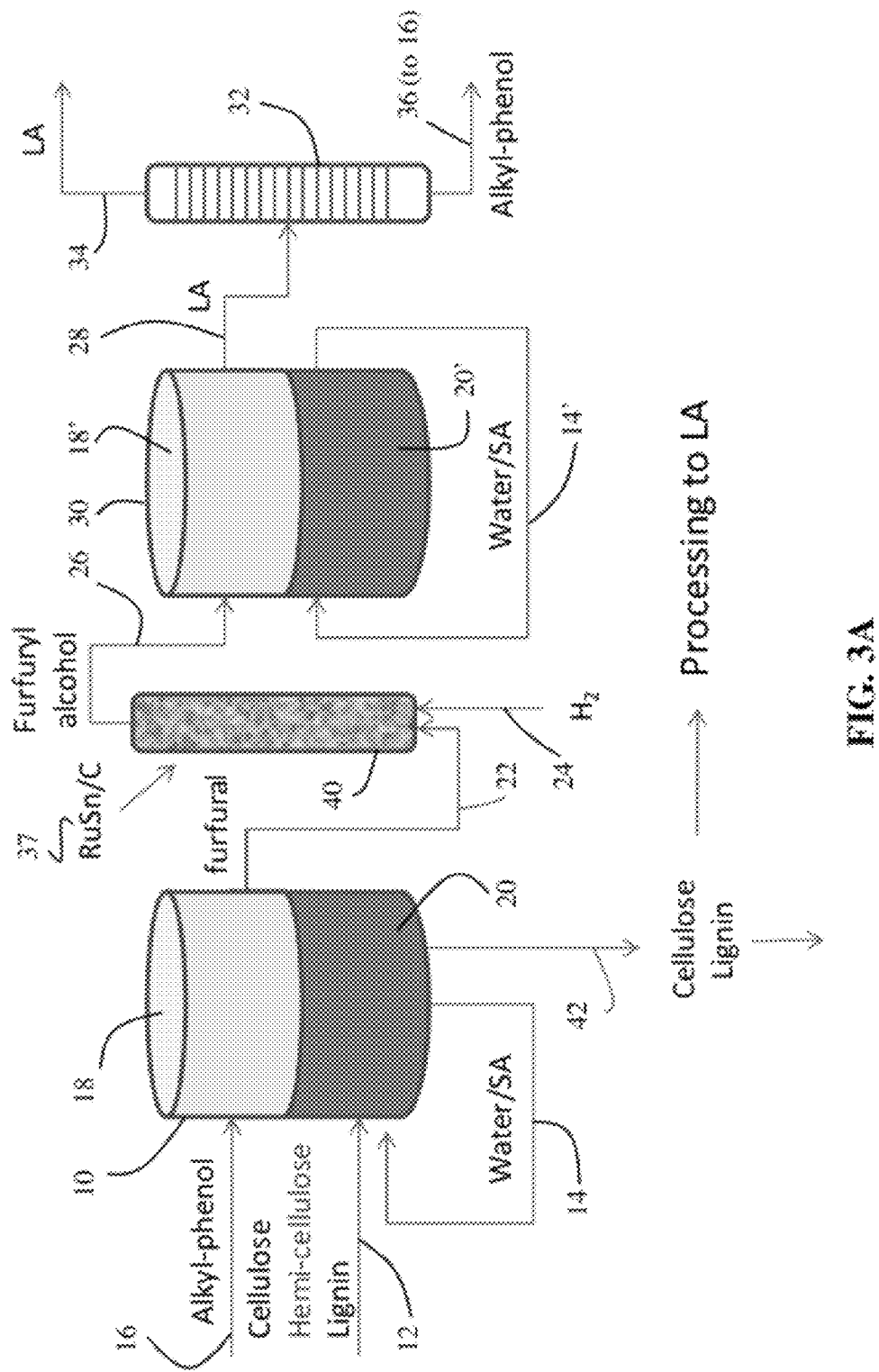
FIG. 3A is a schematic diagram of a first version of the method in which biomass (cellulose, hemicelluloses, lignin) is sequentially converted to furfural, then furfuryl alcohol, and ultimately levulinic acid. The aqueousn solutions ("water/SA") are recycled, as is the alkylphenol extraction solvent.

FIG. 3A illustrates one version of the method which is designed for the preparation of levulinic acid from biomass fractions containing $C_5$ sugars via the formation and isolation of furanic intermediates (furfural) in alkylphenol solvents. In this strategy, incoming biomass is converted, in a step-wise fashion, to furfural, then to furfuryl alcohol, and ultimately to levulinic acid (LA). As shown in FIG. 3A, the method proceeds as follows: Incoming biomass 12 (comprising cellulose, hemicelluloses, and/or lignocelluose) is introduced into a biphasic reactor 10 containing an aqueous acidic reaction medium 20, and an organic AP extraction medium 18. (The AP used in vessel 10 may be introduced via conduit 16, which is charged with recycled AP coming from separator 32 via conduit 36; see below.) As shown in the figure, these two layers spontaneously separate. The $C_5$ fraction of incoming biomass (12) is dehydrated within the acidified aqueous layer (20) to form furfural. Upon formation, furfural so formed is continuously extracted into the non-reactive organic phase containing at least one alkylphenol solvent. The aqueous acid reaction mixture may be recycled to treat additional incoming reactants as shown by recycle conduit 14. Unreacted cellulose and lignins are removed from the system via conduit 42 and may be further processed in a number of strategies.

The furfural so formed may be isolated as a final product, if desired, as described in preceding discussions. Alternatively and without isolation, as considered in FIG. 3A, the furfural may be directed into catalytic reactor 40 via conduit 22, where it is hydrogenated to form furfuryl alcohol. Hydrogen may be supplied to the reactor 40 from an external source (not shown) via conduit 24. The hydrogenation reaction may occur over a metallic hydrogenation catalyst 37, preferably a catalyst comprising platinum and tin on a support. See the definitions, herein, for other hydrogenation catalysts than can be used in the method to convert furfural into furfuryl alcohol. Alternatively, furfural can be converted into furfuryl alcohol by hydrogen transfer using a metal oxide or metal and an appropriate hydrogen donor, see the definitions, hereinabove, for other hydrogen transfer catalysts and hydrogen donors. Importantly, the strategies disclosed herein offer selective conversion of furfural without transformation of alkylphenols used as extracting solvents such that upgrading may occur without isolation from prior reaction media.

In the process depicted by FIG. 3A, the furfuryl alcohol exits reactor 40 via conduit 26, where it is introduced into another biphasic reactor, 30. In the same fashion as reactor 10, reactor 30 contains an aqueous acidic reaction medium 20', and an organic AP extraction medium 18'. As shown in the figure, these two layers spontaneously separate. The incoming furfuryl alcohol from conduit 22 is converted upon contact with the acidic aqueous in layer 20' to form LA, which is preferentially extracted into the organic layer 18'. The aqueous phase and any acid contained therein may be recycled to treat additional incoming furfuryl alcohol as shown by recycle conduit 14'. It is not required to isolate the furfuryl alcohol from the alkylphenol extracting solvent prior to processing for LA formation. Indeed the presence of the alkylphenol extracting phase is an advantage, as it reduces the concentration of the furfuryl alcohol in the reactive aqueous phase, minimizing side reactions to increase the final yield of LA (see examples). Analogously (as described in FIG. 2B), levulinate esters may be formed at this stage through the additional inclusion of an appropriate esterification reagent, such as alcohols and/or olefins.

The LA or LA esters so formed in the method described by FIG. 3A is then transferred from the organic layer 18' to a separator 32 via conduit 28. As noted above, the separator may be any device now known or developed in the future for separating liquids. A distillation apparatus is preferred. The LA or LA esters are thus purified and removed from the separator via conduit 34, while the AP solvent is removed from the separator at conduit 36 and may be recycled back into the system.

Figure 3B:
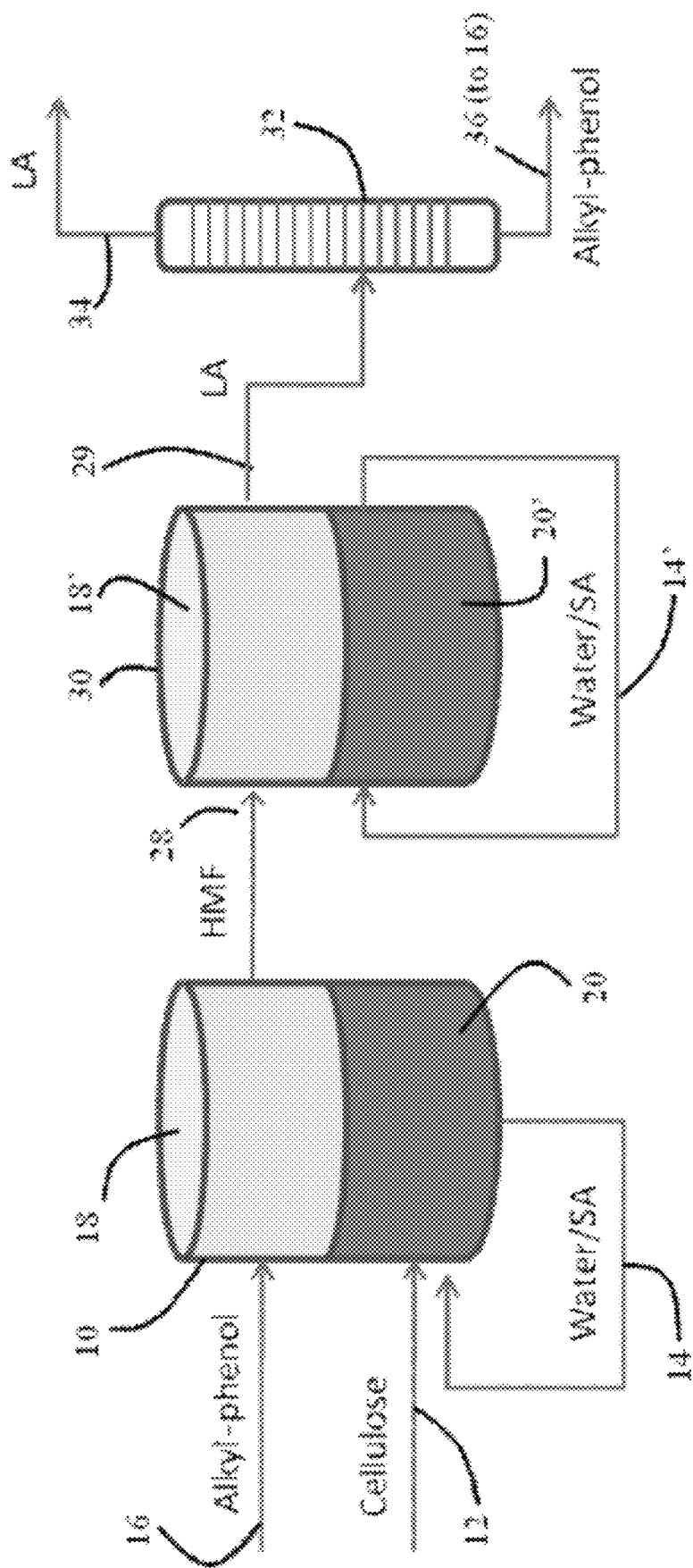
FIG. 3B is a schematic diagram of a method in which biomass (cellulose, hemicelluloses, lignin) is sequentially converted to HMF and then levulinic acid. The aqueous, acid reaction solutions ("water/SA") are recycled, as is the alkylphenol extraction solvent.

FIG. 3B illustrates another version of this method to allow high-yield production of levulinic acid from $C_6$ sugars found in biomass via formation and upgrading of HMF in biphasic systems containing alkylphenol extracting solvents. In this incarnation of the process, $C_6$ sugars contained in incoming biomass are converted, in a step-wise fashion, to hydroxymethylfurfural and then to levulinic acid (LA). As shown in FIG. 3B, the method proceeds as follows: Incoming biomass 12 (comprising cellulose, hemicelluloses, and/or lignocellulose) is introduced into a biphasic reactor 10 containing an aqueous, acidic reaction medium 20, and an organic AP extraction medium 18. (The AP used in vessel 10 may be introduced via conduit 16, which is charged with recycled AP coming from separator 32 via conduit 36; see below.) As shown in the figure, these two layers spontaneously separate. The incoming biomass 12 is converted within the aqueous layer (20) which preferentially contains an acidic catalyst to form hydroxymethylfurfural. The aqueous reaction media and any acid catalyst contained therein may be recycled to treat additional incoming reactants as shown by recycle conduit 14.

The hydroxymethylfurfural so formed may be isolated as a final product, if desired as described in the preceding strategies. Alternatively and without the necessity of isolation from the AP extracting solvent, as shown in FIG. 3B, the hydroxymethylfurfural may be passed into another biphasic reactor 30 via conduit 28. In the same fashion as reactor 10, reactor 30 contains an aqueous acidic reaction medium 20', and an organic AP extraction medium 18'. These two layers spontaneously separate, and HMF is partitioned favorably into the organic phase. The incoming hydroxymethylfurfural from conduit 70 is converted upon contact with the acid in layer 20' into formic acid and LA, which, upon formation, are continuously extracted into the organic layer 18'. The aqueous reaction mixture and any acid catalyst contained therein may be recycled to treat additional incoming hydroxymethylfurfural as shown by recycle conduit 14'.

The LA so formed in an AP extracting solvent may then be transferred from the organic layer 18' to a separator 32 via conduit 29. As noted above, the separator may be any device now known or developed in the future for separating liquids. A distillation apparatus is preferred. The LA is thus purified and removed from the separator via conduit 34, while the AP solvent is removed from the separator at conduit 36 and may be recycled back into the system.

Depending on the amount of reactant added to the aqueous acidic solution, the LA concentration in vessel 30 can be increased to 5-10 wt %. The AP solvent extracts LA and FA without extracting the strong acid in vessel 30 (sulfuric acid as shown in FIG. 3B). The data in Table 2 show that as the concentrations of LA in the aqueous phase increase (entries 1-3), the partition coefficient for extraction of LA by the AP in 30 remains at a value of approximately 2 (when using 2-sec-butylphenol (SBP) as the AP). Using equal masses of organic and aqueous phases, the organic phase extracts approximately 71-78% of the LA. The LA partition coefficient decreases to 1.2 when using n-pentylphenol as the AP (NPP; entry 4) and to 0.8 when using n-hexylphenol as the AP (NHP; entry 5.)

TABLE 2

Partition coefficients using 4 g of aqueous phase (0.5M $H_2SO_4$) and 4 g of AP at 298 K.

| Entry | Aqueous phase (M) | | | Organic phase (g) | Total amount in organic phase (%) | | | Partition coefficient ($C_{ORG}/C_{AQ}$) | | |
|---|---|---|---|---|---|---|---|---|---|---|
| | LA | FA | GVL | AP‡ | LA | FA | GVL | LA | FA | GVL |
| 1 | 0.3 | 0.3 | — | B | 71 | 2 | — | 2.0 | 0.02 | — |
| 2 | 1 | 1 | — | B | 73 | 5 | — | 2.0 | 0.05 | — |
| 3 | 2 | 2 | — | B | 78 | 13 | — | 1.9 | 0.1 | — |
| 4 | 2 | 2 | — | P | 70 | 22 | — | 1.2 | 0.1 | — |
| 5 | 2 | 2 | — | H | 61 | 21 | — | 0.8 | 0.1 | |
| 6 | 2* | | — | B | — | — | 96 | — | — | 22.0 |
| 7 | 2* | | — | P | — | — | 95 | — | — | 10.4 |
| 8 | 2* | | — | H | — | — | 92 | — | — | 7.8 |
| 9 | 2 | 2 | 2 | B | 61 | 23 | 93 | 0.7 | 0.1 | 6.3 |
| 10 | 2 | 2 | 4 | B | 66 | 43 | 92 | 0.6 | 0.2 | 4.0 |
| 11 | 2 | 2 | 4 | P | 68 | 55 | 89 | 0.7 | 0.4 | 2.6 |
| 12 | 2 | 2 | 4 | H | 61 | 50 | 87 | 0.5 | 0.3 | 2.3 |
| 13 | 2 | 4 | 4 | B | 68 | 50 | 92 | 0.6 | 0.3 | 3.3 |
| 14† | 2 | 2 | 4 | B | 68 | 50 | 92 | 0.6 | 0.3 | 3.5 |

Figure 3C:
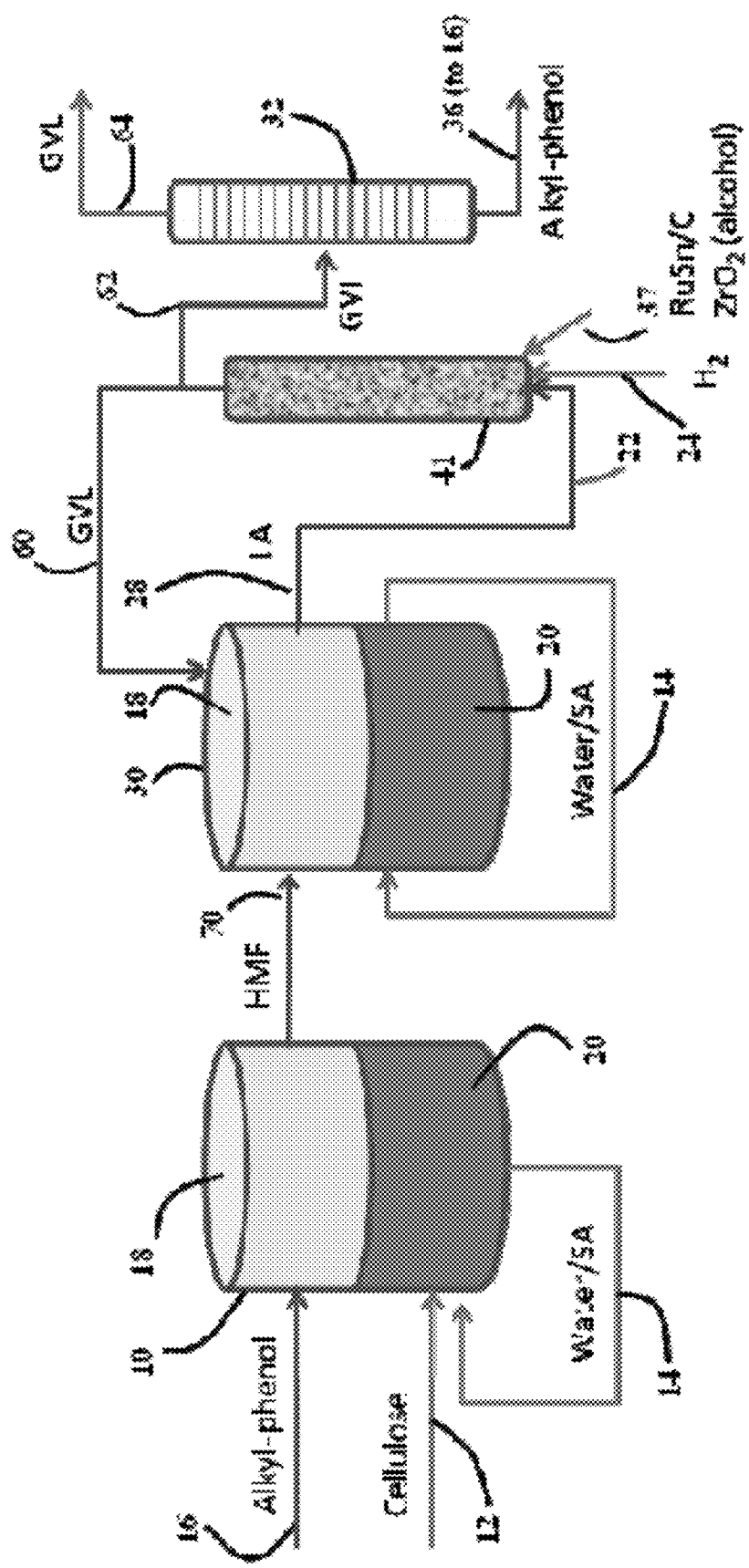
FIG. 3C is a schematic diagram of the method in which biomass (cellulose, hemicelluloses, lignin) is sequentially converted to HMF, levulinic acid, and finally, GVL. The aqueous, acid reaction solutions ("water/SA") are recycled, as is the alkylphenol extraction solvent.

*Aqueous phase is 2M GVL 0.5M $H_2SO_4$.
†at 353 K.
‡B = 2-sec-butylphenol; P = 4-n-pentylphenol; H = 4-n-hexylphenol FIG. 3C shows an alternative version of the process similar to that described in 3B. In this version, rather than isolating LA produced from HMF in a biphasic system, LA is hydrogenated in the presence of AP extracting solvents to yield GVL, which is recovered as a final product. In this approach, instead of isolation, the LA produced from HMF in reactor 30 is transferred from the organic layer to a hydrogenation reactor, 41. In reactor 41, the LA is converted into GVL by hydrogenation. It is preferred that the hydrogenation reaction take place over a metallic hydrogenation catalyst 37, preferably a catalyst comprising ruthenium and tin on a support. Another approach for converting LA to GVL is via hydrogen transfer. Rather than directly hydrogenating the LA, the LA is exposed to a hydrogen donor (typically an alcohol). Rates of GVL production can be enhanced by first converting LA into LA esters (i.e., butyl levulinate) in the presence of an alcohol or olefin and an acid catalyst (not included in FIG. 3C). Catalytic reactors achieving transfer hydrogenation preferably contain a solid metal oxide 37, such as zirconia, alumina, magnesia, titania, etc. which converts the LA esters to GVL in the presence of a hydrogen donor. (See the above for other suitable hydrogen transfer catalysts and hydrogen donors.)

As a unique benefit of this strategy, some or all of the GVL/AP effluent of reactor 41 may be recycled back into reactor 30 via conduit 60 for sequential use as an extracting solvent. This serves to increase the amount of GVL in the ultimate product stream prior to distillation. Once the concentration of GVL has reached a sufficiently high level in the effluent from reactor 41, the effluent stream is directed to separator 32 via conduit 62. The separator 32 has been described previously. The GVL is purified and removed from the separator via conduit 64, while the AP solvent is removed from the separator at conduit 36 and may be recycled back into the system.

Hydrogenation of LA to GVL leads to a decrease in the normal boiling point (from 516 to 479 K), such that GVL is more volatile than SBP (500 K), NPP (538 K), and NHP (560 K). Thus, GVL will be removed from the AP solvent at the top of the distillation column 32, eliminating the need to evaporate the solvent and providing a higher purity product. As the boiling point of the AP solvent increases, the separation of GVL from the solvent requires fewer plates and lower reflux ratios (22). Furthermore, for all AP solvents investigated, the partition coefficient of GVL is higher than for LA (entries 6-8), allowing for the GVL concentration to be increased by successive recycle steps after hydrogenation, as shown by loop 60 in FIG. 3C. However, as the amount of GVL added in the SBP organic phase increases (entries 9 and 10), the LA partition coefficient decreases, such that the organic phase extracted 66% of the LA when a 50/50 mixture of GVL and SBP was used, as compared to 78% extraction of LA when GVL was not present (entry 3). Similar results were obtained with the other AP solvents tested (entries 11 and 12). Thus, the extent of solvent recycle prior to distillation represents a compromise between achieving high concentrations of GVL, while also maintaining a high partition coefficient for LA extraction. Entry 13 in Table 2 shows that a higher FA concentration does not affect the partition coefficients. In the absence of other routes for FA removal, the amounts of FA and LA extracted will become comparable, thus allowing the FA to be used as an internal source of $H_2$ for the reduction of LA to GVL (7).

Another advantage of the high boiling point of the AP solvent is that the extraction can be carried out at elevated temperatures (entry 14), suggesting that the processes presented FIG. 3C (and FIG. 1 to 7, see below) can be carried out at the temperatures employed for biomass deconstruction (e.g., about 420 K), thereby decreasing the need for heat exchangers. This results in energy and equipment savings. In addition, sulfuric acid was not detected in the organic phase for any of the entries in Table 2. Thus, the aqueous phase containing 0.5 M $H_2SO_4$ can be used for multiple steps of cellulose deconstruction.

Regarding the reduction of LA to GVL, previous literature has reported that ruthenium on carbon (Ru/C) is an effective catalyst for converting LA to GVL (10, 11); however, the Ru/C catalyst hydrogenated the C=C bonds in SBP, leading to formation of butyl-cyclohexanone (corresponding to 0.3% conversion of SBP; see Table 6, entry 1 in the examples). In addition, the Ru/C catalyst undergoes deactivation with time-on-stream in the presence of formic acid (FA) (22). As shown in Table 6, the conversion of LA was only 27% and the GVL selectivity was 90.5% over the Ru/C catalyst after 100 h time-on-stream. So while this catalyst will work in the present method, it is not preferred. The LA conversion continues to decrease thereafter. Similar behavior was observed for FA, which is converted to $H_2$ and $CO_2$ (24), such that the FA conversion decreased continuously with time-on-stream (70% conversion at 100 h on-stream). Another limitation of the Ru/C catalyst is that the selectivity for conversion of FA to $CO_2$ is only 75% because of CO methanation reactions (25).

To modify the selectivity of the catalyst to hydrogenate the C=O functional group in LA versus the C=C bonds in SBP, tin was added to the 5 wt % Ru/C in a 3.6:1 Ru:Sn molar ratio. (See Examples.) The addition of Sn eliminated the reduction of SBP for all conditions studied in Table 6 and increased the FA selectivity (>99%) to $H_2$ (26) and $CO_2$. Furthermore, addition of Sn improved catalyst stability, such that the catalyst undergoes slow deactivation over the first 100 h, but then achieves stable performance for more than 230 h with 46% LA and greater than 90% FA conversion (Table 6, entry 2). Moreover, addition of Sn did not negatively affect the GVL production rate, and improved the GVL selectivity by minimizing formation of by-products. Increasing the temperature (entry 3) increased the LA conversion, but decreased the selectivity to GVL, such that the rate of GVL production remained constant.

Decreasing the temperature (Table 6, entry 4) decreased the rate of GVL production, with minimal effect on selectivity. Decreasing the LA and FA concentrations (entry 5) did not significantly affect the GVL production rate, indicating that the rates are of low order with respect to reactant concentrations. The rate of LA conversion is inhibited by the presence of FA, decreasing from 0.30 to 0.09 mmol min$^{-1}$ $g_{cat}^{-1}$ upon addition of FA at 493 K (entries 6 and 2), and decreasing from 0.16 to 0.03 mmol min$^{-1}$ $g_{cat}^{-}$ at 473 K (entry 7 and 4). At both temperatures, the GVL selectivity remained high. Increasing the GVL concentration by successive recycle steps did not affect the GVL production rate. Entry 8 of Table 6 shows that 2 M GVL in the feed did not alter the GVL production rate and only slightly increased the rate of methyltetrahydrofuran (MTHF) production. Therefore, an organic solvent comprising an AP as defined herein and GVL can be used to extract LA without complications in the hydrogenation reactor.

Figure 4:
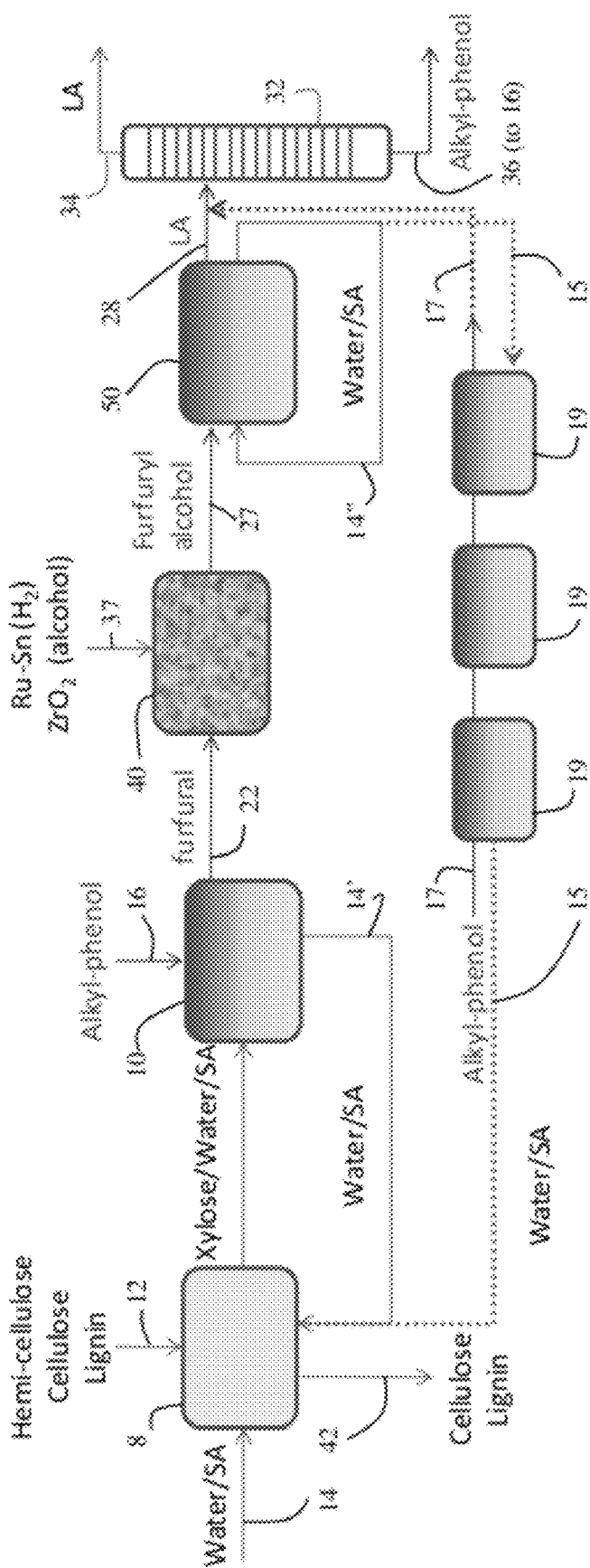
FIG. 4 is a schematic diagram of another version of the method in which the alkylphenol and aqueous reaction solutions are passed through a counter-current extractor to maximize yield of the desired product, in this case, levulinic acid, LA.

FIG. 4 depicts a version of the method similar to that shown in FIG. 3A, with the addition of a series of counter-current extractors 19 to maximize the recovery of LA formed from the deconstruction of the reactant biomass. In FIG. 4, biomass 12 (comprising cellulose, hemicelluloses, and/or lignocellulose) is introduced into a reactor 8 containing an aqueous acidic reaction medium. The aqueous reaction medium enters reactor 8 by one or more of several conduits—fresh acid solution can be introduced via conduit 14, or recycled aqueous acid solution may be introduced into reactor 8 via recycle conduits 14' and/or 15 (see below for more). The acid-catalyzed reaction in vessel 8 yields a solution of xylose, water, and acid (sulfuric acid, SA, is illustrated in FIG. 4) which is passed to reactor 10. Unconverted species (primarily cellulose and lignin) are removed from reactor 8 via conduit 42 and may be directed toward further processing.

The acidic solution of xylose formed in vessel 8 is directed to vessel 10, and contacted with an organic AP extracting solvent, added via conduit 16. (The AP used in vessel 10, introduced via conduit 16, may be recycled AP coming from separator 32 via conduit 36.) As shown in FIG. 4, the aqueous solution containing xylose and acid spontaneously separates from the AP to yield a lower, reactive aqueous layer and an upper organic layer. The xylose in the acidic aqueous layer is dehydrated, forming furfural, which is extracted continuously into the upper organic layer in reactor 10. The acidic aqueous reaction medium may be recycled into vessel 8 for subsequent biomass processing via conduit 14'

The furfural formed in vessel 10 may be isolated as a final product, if desired, as described in preceding scenarios. Alternatively and without isolation from the extracting solvent, as shown in FIG. 4, the furfural may be directed into a catalytic reactor 40 via conduit 22, where it is hydrogenated to form furfuryl alcohol. Hydrogen may be supplied to reactor 40 from an external source (not shown). In reactor 40, the furfural is hydrogenated to yield furfuryl alcohol. It is preferred that the hydrogenation reaction take place over a metallic hydrogenation catalyst 37, preferably a catalyst comprising platinum and tin on a support. See the definitions, hereinabove, for other hydrogenation catalysts than can be used in the method to convert furfural into furfuryl alcohol. Alternatively, furfural can be converted into furfuryl alcohol by hydrogen transfer using a metal oxide and a hydrogen donor, See the definitions, hereinabove, for other hydrogen transfer catalysts and hydrogen donors.

As depicted in FIG. 4, the furfuryl alcohol exits reactor 40 via conduit 27, where it is introduced into another biphasic reactor 50. In the same fashion as reactor 10, reactor 50 contains an aqueous acidic reaction medium (lower layer), and an organic AP extraction medium (upper layer). These two layers spontaneously separate. The incoming furfuryl alcohol from conduit 27 is converted upon contact with an acid catalyst in the aqueous layer of reactor 50 into LA, which is preferentially extracted into the organic layer upon formation. The aqueous reaction mixture and any acid contained therein may be recycled to treat additional incoming furfuryl alcohol as shown by recycle conduit 14". If an alcohol is added into vessel 50, levulinic acid esters are formed instead of levulinic acid and recovered in solution with the alkylphenol. LA or levulinate esters so formed in reactor 50 may then transferred from the organic layer in reactor 50 to a separator 32 via conduit 28. As noted above, the separator may be any device now known or developed in the future for separating liquids. A distillation apparatus is preferred. The LA or levulinate esters are thus purified and removed from the separator via conduit 34, while the AP solvent is removed from the separator at conduit 36 and may be recycled back into the system.

Additionally, a series of counter-current extractors 19 may be employed to maximize recovery of LA. Here, the AP extraction solution from reactors 10 and/or 30 may be passed through counter-current extractors 19 via conduit 17. At the same time, some or all of the aqueous acidic medium being recycled in conduit 14" may be directed by conduit 15 into the counter-current extractors 19, and ultimately recycled back into reactor 8. The AP stream exiting the counter-current extractors 19 is then introduced into the separator 32 via the dashed portion of conduit 17 as shown in the lower right of FIG. 4.

Figure 5:
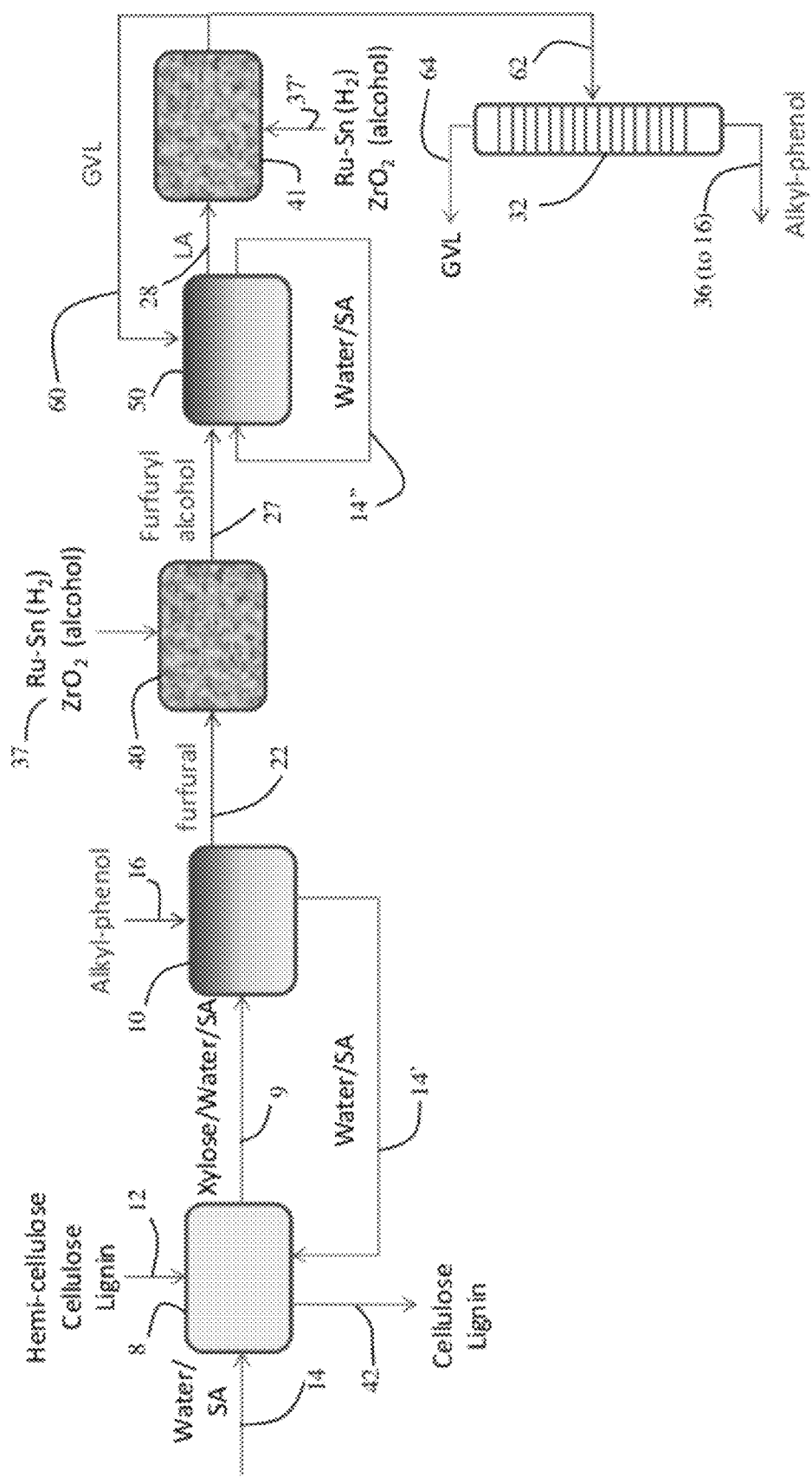
FIG. 5 is a schematic diagram of another version of the method in which the C5 fractions of incoming biomass is sequentially converted to furfural, then furfuryl alcohol, then levulinic acid, and ultimately γ-valerolactone (GVL) while cellulose and lignin are recovered for further processing.

FIG. 5 shows a version of the invention described in 3A by which LA formed from furfural via furfuryl alcohol is further upgraded to yield GVL. (A counter-current extractor 19 as shown in FIG. 4 could also be incorporated into the apparatus schematically illustrated in FIG. 5, but has been omitted for clarity.) In FIG. 5, biomass 12 (comprising cellulose, hemicelluloses, and/or lignocelluose) is introduced into a reactor 8 containing an aqueous acidic reaction medium. The aqueous reaction medium enters reactor 8 by one or more of several conduits—fresh acid solution can be introduced via conduit 14, or recycled aqueous acid solution may be introduced into reactor 8 via recycle conduit 14'. The acid-catalyzed reaction in vessel 8 yields a solution of xylose, water, and acid (sulfuric acid, SA, is illustrated in FIG. 5) which is passed to reactor 10. Unconverted reactants, primarily cellulose and lignin, are removed from reactor 8 via conduit 42 and may be further processed.

The acidic solution of xylose formed in vessel 8 is directed to vessel 10, and an organic AP extracting solvent is added via conduit 16. (The AP used in vessel 10, introduced via conduit 16, may be recycled AP coming from separator 32 via conduit 36.) As shown in FIG. 5, the aqueous solution containing xylose and acid spontaneously separates from the AP to yield a lower aqueous layer and an upper organic layer. The xylose in the aqueous layer undergoes dehydration in the lower, acidic aqueous layer to form furfural, which is continuously extracted into the upper organic layer in reactor 10. The aqueous reaction medium and any acid catalyst contained therein may be recycled into vessel 8 via conduit 14'

The furfural formed in vessel 10 may be isolated as a final product, if desired, as described in the preceding scenarios. Alternatively, as shown in FIG. 5, the furfural may be directed into a catalytic reactor 40 via conduit 22, where it is hydrogenated to form furfuryl alcohol. Hydrogen may be supplied to reactor 40 from an external source (not shown). It is preferred that the hydrogenation reaction take place over a metallic hydrogenation catalyst 37, preferably a catalyst comprising platinum and tin on a support. Hydrogenation may also be accomplished by a hydrogen transfer reaction (described below). See the definitions, hereinabove, for other hydrogenation catalysts than can be used in the method to convert furfural into furfuryl alcohol.

The furfuryl alcohol so formed exits reactor 40 via conduit 27, where it is introduced into another biphasic reactor 50. In the same fashion as reactor 10, reactor 50 contains an aqueous acidic reaction medium (lower layer), and an organic AP extraction medium (upper layer). These two layers spontaneously separate. The incoming furfuryl alcohol from conduit 27 is converted upon contact with the acidic layer in reactor 50 into LA, which is preferentially extracted into the organic layer. The aqueous reaction mixture and any acid catalyst contained therein may be recycled to treat additional incoming furfuryl alcohol as shown by recycle conduit 14". If an alcohol is added into vessel 50, levulinate esters are formed instead of levulinic acid and are recovered in an organic phase composed primarily of alkylphenol solvents.

The LA or levulinic acid ester is then transferred with or without isolation from the organic layer in reactor 50 to another hydrogenation reactor, 41, which is analogous to the reactor 40. In reactor 41, the LA or levulinate esters are converted into GVL. It is preferred that the hydrogenation reaction take place over a metallic hydrogenation catalyst 37', preferably a catalyst comprising ruthenium and tin on a support. Another approach for converting LA to GVL is via hydrogen transfer. Rather than directly hydrogenating the LA, the LA is exposed to a hydrogen donor (typically an alcohol) in presence of a metal oxide as catalyst. Rates can be enhanced converting previously the LA into esters LA esters (i.e., levulinate esters) in the presence of an alcohol and an acid catalyst. This results in a biphasic system in which the lower, aqueous phase contains water, alcohol, and the strong acid used to make the esters, and the upper, organic layer contains levulinate esters and AP. The water/alcohol/acid solution can be recirculated as described previously. The upper layer containing the LA esters and AP is transferred to a reactor such as reactor 41 in FIG. 5. The reactor preferably contains a solid metal oxide, such as zirconia, alumina, magnesia, titania, etc. that converts the LA esters to GVL. (See the above for other suitable hydrogen transfer catalysts and hydrogen donors.) The GVL so formed may be then processed as described previously, i.e., via distillation or reactive upgrading. See the description of FIG. 5 for further details. The catalysts 37 and 37' may be the same or different. Some or all of the GVL formed in reactor 41 may be recycled along with the AP extracting solvent back into reactor 50 via conduit 60 to increase the amount of GVL in the ultimate product stream. Once the concentration of GVL has reached a sufficiently high level in the effluent from reactor 41, the effluent stream is directed to separator 32 via conduit 62. The separator 32 has been described previously. The GVL is purified and removed from the separator via conduit 64, while the AP solvent is removed from the separator at conduit 36 and may be recycled back into the system.

Figure 6:
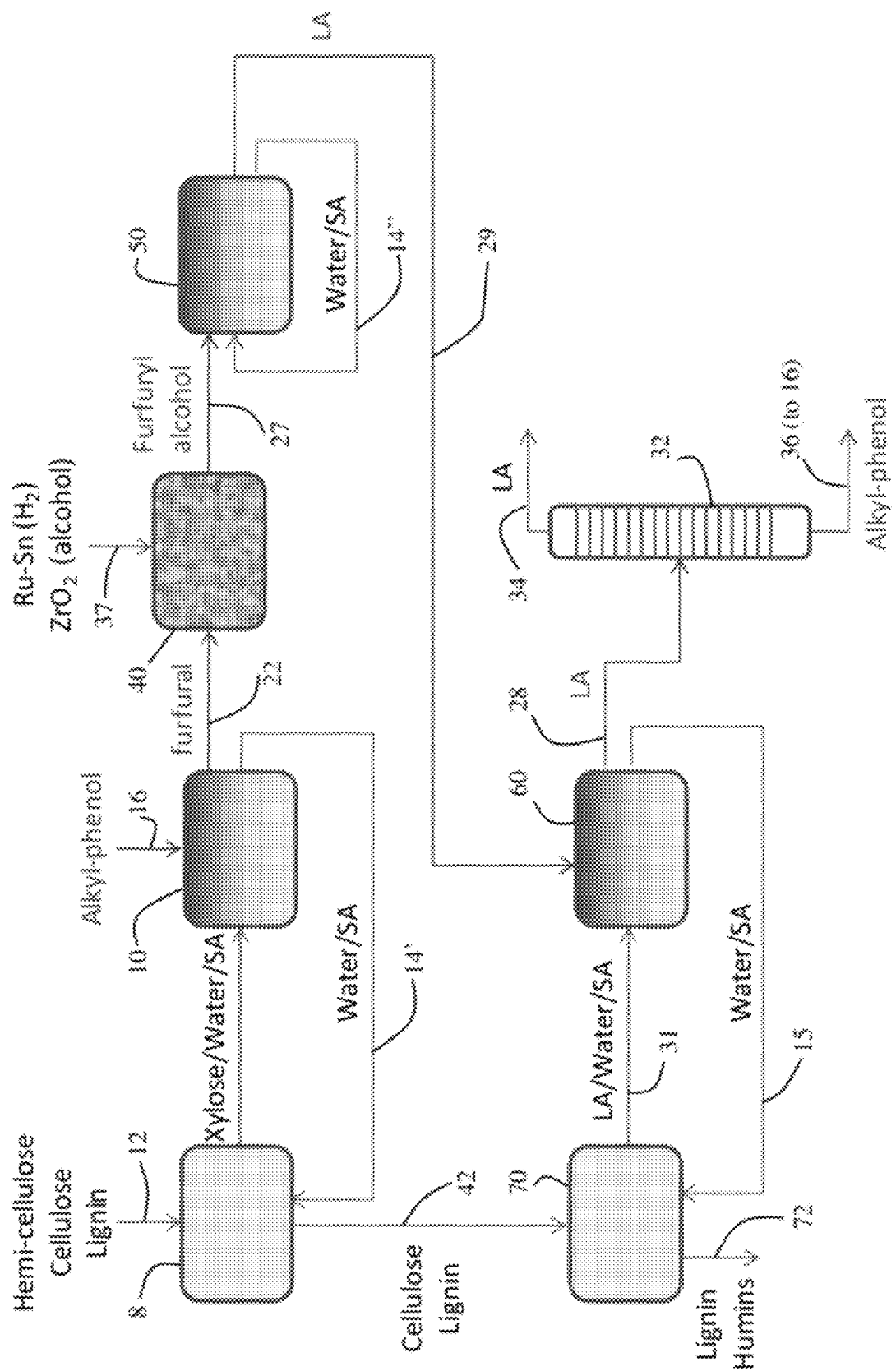
FIG. 6 is a schematic diagram of another version of the method in which the C5 and C6 fractions of incoming biomass are processed in parallel strategies to form of levulinic acid. In this strategy, both the AP extraction solution and the aqueous, acidic reaction solution are recycled for further use.
Figure 7:
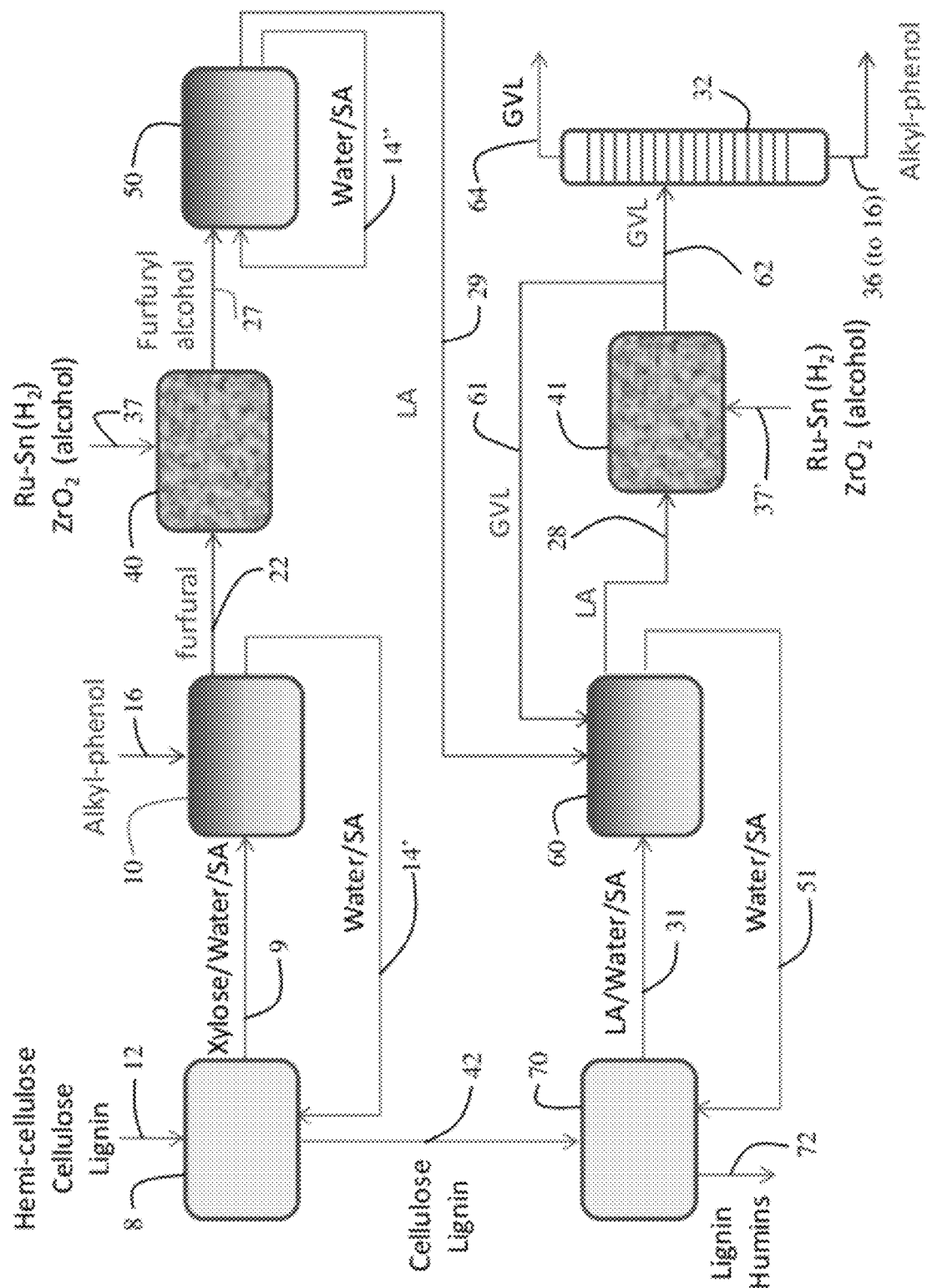
FIG. 7 is a schematic diagram of another version of the invention, similar to the version shown in FIG. 6, except that the levulinic acid so formed is further reacted to yield GVL prior to distillation.

FIGS. 6 and 7 show alternative, closed loop methods to make LA (FIG. 6) and/or GVL (FIG. 7). Importantly, these ultimate embodiments of the technology disclosed herein offer integrated strategies by which production of common intermediate platform chemicals (furans, LA, or GVL) may be achieved in parallel from both $C_5$ and $C_6$ biomass fractions. In FIGS. 6 and 7, biomass 12 is introduced into a reactor 8 containing an aqueous acidic reaction medium. The aqueous reaction medium enters reactor 8 via recycling conduit 14'. The acid-catalyzed reaction in vessel 8 yields a solution of xylose, water, and acid which is passed to reactor 10. Unconverted reactants, comprised of cellulose and lignin, are removed from reactor 8 via conduit 42 and are subjected to further processing as described below.

An organic, AP extracting solvent is added to the xylose, water, and acid solution in vessel 10 via conduit 16. (The AP used in vessel 10, introduced via conduit 16, may be recycled AP coming from separator 32 via conduit 36.) As shown in FIGS. 6 and 7, the aqueous solution containing xylose and acid spontaneously separates from the AP to yield a lower aqueous layer and an upper organic layer. The xylose in the aqueous layer undergoes dehydration in the lower, acidic aqueous layer to form furfural, which is extracted into the upper organic layer in reactor 10. The aqueous reaction medium and any acid catalyst contained therein may be recycled into vessel 8 via conduit 14'

The furfural formed in vessel 10 may be isolated as a final product, if desired. Alternatively, as shown in FIGS. 6 and 7, the furfural may be passed into catalytic reactor 40 via conduit 22, where it is hydrogenated to form furfuryl alcohol. Hydrogen may be supplied to reactor 40 from an external source (not shown). It is preferred that the hydrogenation reaction take place over a metallic hydrogenation catalyst 37, preferably a catalyst comprising platinum and tin on a support. See the definitions, hereinabove, for other hydrogenation catalysts than can be used in the method to convert furfural into furfuryl alcohol. Alternatively furfural can be converted into furfuryl alcohol by hydrogen transfer using a metal oxide and an appropriate hydrogen donor, see the definitions, hereinabove, for other hydrogen transfer catalysts and hydrogen donors.

The furfuryl alcohol exits the reactor 40 via conduit 27, where it is introduced into another biphasic reactor 50. In the same fashion as reactor 10, reactor 50 contains an aqueous acidic reaction medium (lower layer), and an organic AP extraction medium (upper layer). These two layers spontaneously separate. Furfuryl alcohol from conduit 27 is converted upon contact with the acidic, aqueous layer in reactor 50 into LA, which is preferentially extracted into the organic layer. The aqueous reaction mixture and any acid catalyst contained therein may be recycled to treat additional incoming furfuryl alcohol as shown by recycle conduit 14". Alternatively, levulinate esters may be formed by previously considered modifications to this strategy.

As shown in both FIGS. 6 and 7, LA or levulinate esters may be transferred to another vessel 60 containing both an aqueous reaction solution and an AP extraction solvent. The aqueous acidic solution in vessel 60 is supplied from vessel 70, which is connected via conduit 70 to the original reaction vessel 8. As shown in FIGS. 6 and 7, unconverted reactants from vessel 8 are transferred via conduit 42 into vessel 70 for further acid-catalyzed reaction to convert residual cellulose to LA. The acidic aqueous reaction solution in vessel 70 is supplied by recycling loop 15. The final waste from the method, composed mostly of lignin and humins is removed from vessel 70 via conduit 72. The acidic aqueous reaction mixture, containing levulinic and sulfuric acids in water, is transferred from vessel 70 to vessel 60 via conduit 31. In vessel 70, it is contacted with an organic phase containing an AP extracting solvent and levulinic acid produced in vessel 50. As described previously, most of the LA present in the aqueous medium exiting vessel 70 is extracted into the AP extraction solvent contained in vessel 60.

FIGS. 6 and 7 differ in the ultimate fate of the LA. In FIG. 6, the LA is the final product, and it is isolated from the extracting solvent. In FIG. 7, the LA is upgraded to GVL without isolation of the LA from the extracting solvent. Thus, in FIG. 6, the LA is then transferred from the organic layer in reactor 60 to a separator 32 via conduit 28. As noted above, the separator may be any device now known or developed in the future for separating liquids. A distillation apparatus is preferred. The LA is thus purified and removed from the separator 32 via conduit 34, while the AP solvent is removed from the separator at conduit 36 and may be recycled back into the system.

In FIG. 7, the LA is introduced into a reactor 41 via conduit 28. The reactor 41 contains a hydrogenation catalyst 37' as described previously. The catalyst is dimensioned and configured to reduce the LA into GVL. The GVL so formed is then transferred to separator 32 via conduit 62. The GVL is purified and removed from the separator 32 via conduit 64, while the AP solvent is removed from the separator at conduit 36 and may be recycled back into the system.

EXAMPLES

The following Examples are included solely to provide a more complete disclosure of the method described and claimed herein. The Examples do not limit the scope of the claims in any fashion.

Example 1

Dehydration of Xylose to Furfural

Dehydration of xylose in aqueous solutions to obtain furfural was carried out using mineral acids, such as HCl. An organic extracting solvent, 2-sec-butylphenol (SBP), was used to extract furfural continuously to separate it from xylose and the mineral acid and to inhibit further degradation. The partition coefficient of furfural in a mixture SBP/water (ratio of the furfural concentration in SBP to the furfural concentration in water) is 35. The experiments were carried out in 10 mL glass reactors at 170° C. in a pre-heated oil bath using magnetic stirring.

In a typical experiment, aqueous xylose solutions of varied concentration were prepared. Typically, the HCl concentration in the aqueous phase was 0.1M HCl. The aqueous xylose solution and SBP were added into the glass reactor to reach the desired mass ratio (aqueous layer (g)/SBP (g)). To end the reactions, the glass reactors were taken out from the oil bath and cooled in an ethylene glycol/dry ice bath. The two phases were then separated and analyzed to quantify furfural and xylose using GC and HPLC for organic and aqueous phase analyses, respectively. Xylose conversion, furfural selectivity/yield, and furfural distribution values for experiments with 10% xylose feed with 0.1M HCl at 170° C. at times ranging from 30-120 min are shown in Table 3. The mass ratio of xylose solution to SBP was kept at 0.5 for these experiments by using 2 g of aqueous solution with 4 g of SBP. For all cases 99% of furfural was retained in SBP. The maximum yield achieved is 71%. It was found that the furfural yield could be improved by adding salt (NaCl) to the aqueous phase. In those experiments, after reaching 0.1M HCl concentration in xylose solutions, the aqueous feed was saturated with NaCl. It can be seen in Table 3 that the added salt increases the xylose dehydration rate as well as the furfural degradation rate. The furfural selectivity decreases with increasing xylose conversion resulting in a 78% maximum yield at 15 min reaction time.

A high partition coefficient of furfural in the water-SBP system allowed reaching high yields of furfural even when the mass ratio of the aqueous solution to SBP was increased. This way, higher concentrations of furfural compared to starting xylose concentrations were obtained in a single stage. This is particularly advantageous, because only 1-2 wt. % aqueous xylose solutions can be obtained from raw biomass (e.g., corn stover) with dilute acid treatments. As shown in Table 3, starting with 1.5 wt % xylose feed (0.1M HCl, saturated with NaCl) and using low relative amounts of SBP (ratio of xylose solution mass-to-SBP mass=6.67), high yields of furfural (78%) were reached with 93% of furfural partitioning to SBP, thus resulting in a 4.1 wt. % furfural in SBP. Increasing the concentration of furfural in the product mix is particularly desired for downstream processing options, such as distillation or further upgrading reactions.

Experiments were also carried out using the aqueous xylose solution obtained from dilute acid treatment of corn stover with 0.1M HCl solution saturated with NaCl. 1.1 wt % xylose solution is obtained following the acid treatment at 100° C. for 5 h. The result of the dehydration experiment at 170° C. for 15 min using an aqueous solution to SBP mass ratio of 6.67 is shown in Table 3.

TABLE 3

Results of xylose dehydration experiments carried out at 170° C. in a biphasic system, using SBP as the extracting solvent.

| Catalyst/salt | Xylose wt. % | xylose soln (g)/ SBP(g) | Time (min) | Xylose conversion (%) | Furfural Selectivity (%) | Furfural Yield (%) | % Furfural in SBP | Final furfural wt % in SBP |
|---|---|---|---|---|---|---|---|---|
| 0.1M HCl/ no salt | 10 | 0.5 | 30 | 69 | 68 | 47 | 99 | 1.4 |
| | | | 60 | 96 | 74 | 71 | 99 | 2 |
| | | | 120 | 99 | 71 | 70 | 99 | 2 |
| 0.1M HCl/ NaCl | 7.7 | 0.5 | 10 | 81 | 86 | 70 | 99 | 1.6 |
| | | | 15 | 98 | 80 | 78 | 99 | 1.8 |
| | | | 20 | 100 | 71 | 71 | 99 | 1.6 |
| 0.1M HCl/ NaCl | 1.5 | 6.67 | 10 | 69 | 78 | 54 | 93 | 3 |
| | | | 15 | 92 | 83 | 76 | 94 | 4 |
| | | | 20 | 98 | 80 | 78 | 93 | 4.1 |
| | | | 30 | 100 | 71 | 71 | 93 | 3.7 |
| 0.1M HCl/ NaCl | Xylose feed obtained from corn stover (1.2%) | 6.67 | 15 | 77 | 85 | 63 | 93 | 3.2 |

Example 2

Dehydration of Fructose to Hydroxymethylfurfural

Dehydration of fructose in aqueous solutions to obtain 5-hydroxymethylfurfural (HMF) is carried out using mineral acids, such as HCl. An organic extracting solvent, 2-sec-butylphenol (SBP), is used to extract HMF continuously to separate it from fructose and the mineral acid and to inhibit further degradation. The experiments were carried out in 10 mL glass reactors at 170° C. in a pre-heated oil bath using magnetic stifling. In a typical experiment, an aqueous fructose solution with a desired weight percentage was prepared to obtain a 0.1 M HCl and saturated with NaCl. The aqueous fructose solution and SBP were added into the glass reactor to reach the desired mass ratio (aqueous layer (g)/SBP (g)). To end the reactions, the glass reactors were taken out from the oil bath and cooled in an ethylene glycol/dry ice bath. The two phases were then separated and analyzed to quantify HMF and fructose using HPLC. Using 1.5 g of aqueous solution (7.8% fructose) and 3 g of SBP, at 170° C., in 5 min, 74% yield of HMF was obtained with complete conversion of fructose. 97% of HMF was retained in SBP. Short residences times are used to minimize the conversion of HMF to LA in this step.

Example 3

Hydrogenation of Furfural to Furfuryl Alcohol Using Metal Catalyst

Liquid phase reduction of furfural to furfuryl alcohol in 2-sec-butylphenol (SBP) takes place with molecular hydrogen over a Pt—Sn bimetallic catalyst supported on $SiO_2$ support. Silica-supported Pt/Sn catalysts were prepared by sequential impregnation according to Dumesic et al (Catal. Today 2000, 55, 213) to reach 3:1 ratio of Pt:Sn. Platinum was added to Cab-O-Sil-brand fumed silica (Cabot Corp., Boston, Mass.) by incipient wetness impregnation. Tin was added to the $Pt/SiO_2$ catalyst by evaporative impregnation of a solution of tributyltin acetate in pentane. After impregnation with tin, the catalysts were dried at 373 K, calcined with flowing air at 573 K (2 h), followed by reduction in flowing hydrogen at 773 K (2 h).

Figure 12:
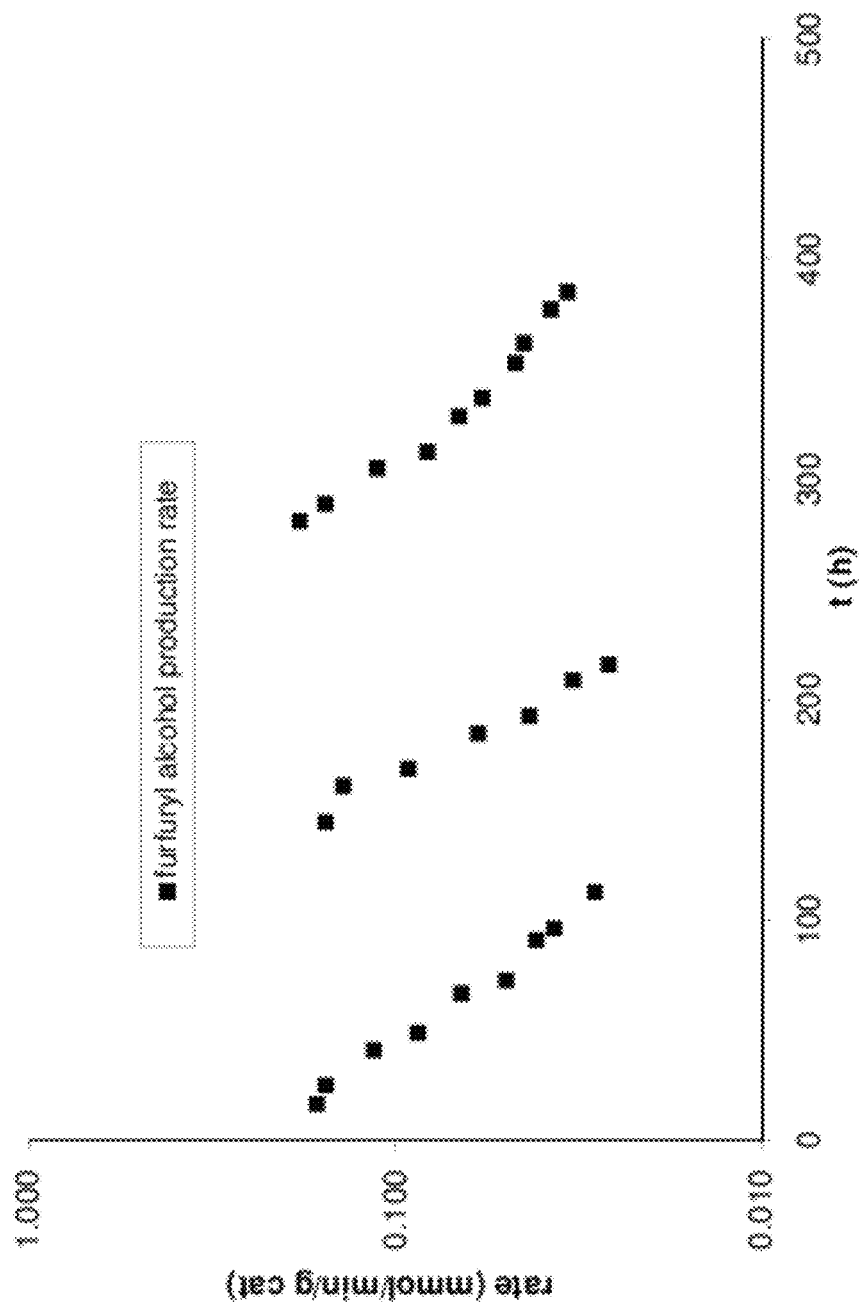
FIG. 12. Rate of furfuryl alcohol production over Pt—Sn/$SiO_2$ (Pt:Sn=3:1) at 373 K and 500 psig $H_2$ pressure with 5 wt. % furfuryl alcohol in SBP. First regeneration (calcination in air at 573 K) was carried out after 112 h time on stream and the second was performed after 216 h time on stream.

A fixed bed, down-flow reactor consisting of a half-inch stainless steel tube was used for all experiments. Quartz wool was used in the lower end of the reactor to keep the catalyst bed in place. Both catalysts were mixed with crushed fused $SiO_2$ granules (Aldrich) in a 1:1 volumetric ratio to maintain constant bed height. The reactor was surrounded with an aluminum block that was heated externally by a well-insulated furnace (Applied Test Systems). Type-K thermocouples (Omega) were used to measure the reaction temperature, which was controlled by a PID controller (Love controls) connected to a variable transformer (Tesco). Mass flow controllers (Brooks 5850E) were used to regulate the flow of $H_2$ during the experiments. The liquid feed was pumped from a graduated cylinder by an HPLC pump (Lab Alliance series 1) to a needle located at the entrance of the catalyst bed. A back-pressure regulator (GO model BP-60) was used to control the total pressure, which was measured by two gauges at the entrance and the exit of the bed. A gas-liquid separator at room temperature was used to collect the liquid effluent phase for analysis. After the reduction was completed, the temperature (373 K) and pressure (500 psig) were adjusted and the feed flow (0.04 mL/min) was started with flowing $H_2$ (30 mL/min) for reactions. The feed used was 5 wt % furfural in SBP and Pt—$Sn/SiO_2$ (0.1 g, Pt:Sn=3:1) was used as the catalyst. Quantification of furfural and furfuryl alcohol were performed using a gas chromatograph (Shimadzu GC-2010; Shimadzu Scientific Instruments, Columbia, Md.) equipped with a flame-ionization detector (FID). With a fresh catalyst, 98.8% conversion of furfural can be achieved with 97.8% selectivity towards furfuryl alcohol. The furfuryl alcohol production rate at this point is 0.18 mmol/min/g cat. SBP was not converted during the reaction and behaved as an inert diluent. As shown in FIG. 12, deactivation of Pt—Sn catalyst is observed with time on stream, even though the selectivity to furfuryl alcohol stays the same. However, the catalytic activity can be regained fully by calcining the Pt—Sn/$SiO_2$ with air at 573 K. FIG. 12 shows the furfuryl alcohol production rate with time on stream for fresh catalyst as well as after 2 regeneration treatments.

Example 4
Hydrogenation of Furfural to Furfuryl Alcohol by Hydrogen Transfer Liquid phase reduction of furfural to furfuryl alcohol can be carried out using a hydrogen donor and metal oxide catalyst as $ZrO_2$. The $ZrO_2$ catalyst was prepared by precipitation of $ZrO(NO_3)_2$ with $NH_4OH$ (Aldrich), according to Serrano-Ruiz et al. (*J. Catal.*, 241, (2006), 45-55). Solids were calcined 60 $cm^3$ (STP)/min flowing air at 723 K for 4 h prior to use in batch experiments. Quantification was performed using a gas chromatograph (Shimadzu GC-2010; Shimadzu Scientific Instruments, Columbia, Md.) equipped with a flame-ionization detector (FID). Identification of products in the liquid phase was performed using a gas chromatograph-mass spectrometer (Shimadzu Corp., GCMS-QP2010S) equipped with a Rxi®-brand SHRXI-5MS capillary column (30 m×0.25 mm×0.25 µm) (Restek Corporation, Bellefonte, Pa.).

The reactions were performed in a 50 mL batch reactor (Parr Instruments). For all experiments, the feed was 5 wt % furfural in a solvent (solvent composition is described in Table 4) and $ZrO_2$ was used as the catalyst. Reactor contents were pressurized under 300 psi He prior to heating to the reaction temperature. In all cases, the alkylphenol, 2-sec butylphenol (SBP) was not converted during the reaction and behaved as an inert diluent. As shown in Table 4, the yield of furfuryl alcohol is higher at lower reaction temperatures. Also, selectivities to furfuryl alcohol and the specific reaction rates are higher when (isopropanol) IPA and (2-butanol (2BuOH) are used as the hydrogen donors as compared to 2-hexanol (2HO)

Example 5
Conversion of Furfuryl Alcohol to Levulinic Acid and Levulinate Esters Conversion of furfuryl alcohol to levulinic acid/ester is carried out using mineral acids, such as HCl and $H_2SO_4$, as well as a solid acid catalysts, such as Amberlyst-15. When the desired product is levulinic acid, the reaction is carried out in a biphasic system that consists of the organic layer (furfuryl alcohol in SBP) and an aqueous layer (containing the acid catalyst, such as 1 M $H_2SO_4$ or Amberlyst-15)). The experiments were carried out in 10 mL glass reactors at 125° C. in a pre-heated oil bath using magnetic stirring. In a typical experiment, aqueous solution and organic solution were added into the glass reactor to reach the desired volume ratio (organic (mL)/aqueous (mL)). To end the reactions, the glass reactors were taken out from the oil bath and cooled in an ethylene glycol/dry ice bath. The two phases were then separated and analyzed to quantify levulinic acid and furfuryl alcohol using GC and HPLC for organic and aqueous phase analyses, respectively. While only 50% yield of levulinic acid is obtained in a single aqueous phase medium with 1M $H_2SO_4$, up to 76% yield can be obtained when the furfuryl alcohol is introduced in SBP. The SBP minimizes the concentration of the furfuryl alcohol in the aqueous phase releasing slowly from the organic phase as it is converted to LA. Levulinic acid yields for the bi-phasic SBP-water system at 125° C. using different catalysts, reaction times, feed concentrations and organic/aqueous volume ratio are given in Table 5. When the volume ratio of organic to aqueous layer is 1, around 73% of levulinic acid can be retained in the SBP layer. However, as shown in Table 5, by decreasing the amount of aqueous layer to obtain a ratio of 2, more (86%) levulinic acid can be recovered in the organic layer, while still reaching around 71% total yield. Further decreases in the aqueous amount, results in retaining most of the levulinic acid in the organic layer (94%); however, the overall yield is decreased further (64%).

When the desired end product is the levulinate ester, the alcohol reactant (primary or secondary) is mixed with the furfuryl alcohol feed in SBP and reacted using a solid acid catalyst, like Amberlyst-15. The experiments were carried out

TABLE 4

Catalytic transfer hydrogenation of furfural to furfuryl alcohol over $ZrO_2$ using various secondary alcohols as the hydrogen donor in the presence of sec-butylphenol.

| Solvent (g:g) | Furfural:$ZrO_2$ (g:g) | Time (h) | T (° C.) | Furfural conversion (%) | Furfuryl alcohol selectivity (%) | Specific rate ($\mu$molg$^{-1}$ min$^{-1}$) |
|---|---|---|---|---|---|---|
| 2BuOH:SBP = 1:1 | 1:1 | 12 | 90 | 51 | 96 | 9 |
| 2BuOH:SBP = 1:4 | 1:1 | 12 | 90 | 26 | 83 | 28 |
| 2BuOH:SBP = 1:1 | 1:1 | 8 | 120 | 89 | 94 | 24 |
| 2BuOH:SBP = 1:1 | 1:1 | 8 | 150 | >99 | 84 | — |
| IPA:SBP = 1:5* | 1:1 | 16 | 120 | 82 | 82 | 11 |
| IPA:SBP = 1:5* | 1:1 | 16 | 150 | >99 | 62 | — |
| IPA:SBP = 1:5* | 1:1 | 8 | 150 | 93 | 69 | 24 |
| 2HO:SBP = 1:4 | 1:1 | 12 | 120 | 37 | 64 | 7 |
| 2HO:SBP = 1:4 | 1:4 | 12 | 120 | 86 | 59 | 3 |
| 2HO:SBP = 1:1 | 1:1 | 12 | 120 | 53 | 75 | 10 |
| 2HO:SBP = 1:1 | 1:1 | 12 | 150 | 86 | 48 | 16 |

*Molar ratio of furfural:IPA = 1:5 in 50 mL batch reactors (PARR instruments) at 110° C. Compared to a pure alcohol solvent, the presence of SBP in 50%-50% weight mixture with alcohol decreases the yield to the ester from furfuryl alcohol. Primary alcohols result in higher yields towards the ester. When secondary alcohols are used, the dehydration of the alcohol to corresponding alkenes becomes significant. The results are represented in Table 5.

2 hours before loading into a flow reactor, or reduced for 3 h at 723 K (1 K min$^{-1}$) and passivated in 2% $O_2$/He for 3 hours before use in a batch reactor. For the Ru/C catalysts impregnated by copper, copper (II) nitrate hemipentahydrate was used as the copper source, and the procedure above was followed. The Ru:Cu atomic ratio varied from 1:9 to 3:1.

TABLE 5

Yield to levulinic acid/ester starting from furfuryl alcohol solutions in 2-sec-Butylphenol (SBP) in a bi-phasic system with water or a single phase system with alcohols. LA, BL, SA and A-15 correspond to levulinic acid, 2-butyl levulinate, sulfuric acid and Amberlyst-15, respectively.

| Furfuryl alcohol wt % | Solvent | org/aq (mL/mL) | T (° C.) | catalyst | t (h) | Yield to LA/ester (%) | % LA in org | Butene loss (%) | Butene/BL |
|---|---|---|---|---|---|---|---|---|---|
| 1 | water | — | 125 | 1M SA | 1 | 49 | — | — | — |
| 1 | SBP-water | 1 | 125 | 1M SA | 1 | 73 | 73 | — | — |
| 1 | SBP-water | 1 | 125 | 1M HCl | 1 | 70 | 72 | — | — |
| 1 | SBP-water | 1 | 125 | 0.1 g A15 | 1 | 76 | 67 | — | — |
| 1 | SBP-water | 1 | 125 | 1M SA | 3 | 76 | 73 | — | — |
| 1 | SBP-water | 2 | 125 | 1M SA | 1 | 71 | 86 | — | — |
| 1 | SBP-water | 4 | 125 | 1M SA | 1 | 64 | 94 | — | — |
| 10 | SBP-water | 1 | 125 | 1M SA | 1 | 35 | 63 | — | — |
| 1 | 2-butanol | — | 110 | 0.5 g A15 | 12 | 71 | — | 9.5 | 82.5 |
| 1 | 50% SBP-50% 2-butanol | — | 110 | 1 g A15 | 6 | 51 | — | 11 | 50.2 |

Example 6

Conversion of HMF to LA and Formic Acid

The conversion of 5-hydroxymethylfurfural (HMF) to levulinic acid and formic acid is carried out using mineral acids, such as sulfuric acid. An organic extracting solvent, 2-sec-butylphenol (SBP), is used to keep the HMF concentration in the aqueous acidic phase low to minimize polymerization side reactions. In addition, SBP extracts the product, LA, continuously to separate it from the mineral acid and inhibit further degradation. The experiments were carried out in 10 mL glass reactors at 150° C. in a pre-heated oil bath using magnetic stirring. In a typical experiment, an HMF solution in SBP with desired weight percentage was prepared and added along with 1 M sulfuric acid (aq.) to the glass reactor to reach the desired volume ratio (aqueous layer (mL)/organic layer (mL)). To end the reactions, the glass reactors were taken out from the oil bath, cooled to room temperature in flowing air and allowed to phase separate overnight. Aqueous and organic phases were then separated and analyzed to quantify LA using a GC and HMF using HPLC. Using 2 mL aqueous solution and 2 mL SBP with the desired concentration of HMF, at 150° C., in 1 hour, roughly 90% yield of LA was obtained with complete conversion of HMF from SBP solutions containing 1 and 5 wt % HMF. 67% of the LA product was retained in the SBP. In 3 hour runs, similar yields were achieved suggesting that levulinic acid, once formed, is stable in such biphasic systems.

Example 7

Hydrogenation of Levulinic Acid to GVL Using Metal Catalyst

The 5 wt % Ru/C was used as received from the vendor (Sigma-Aldrich). The Ru—Sn/C catalyst was prepared by incipient wetness impregnation of the 5 wt % Ru/C catalyst with a solution of 5 $nCl_2.2H_2O$, which resulted in a final molar ratio Ru:Sn of 3.6:1. The catalyst was dried at 353 K for Hydrogenation of LA was carried out in a fixed-bed reactor operating in an up-flow configuration. The catalyst was placed in a stainless steel tubular reactor (6.35 mm OD) and held between two end plugs of silica granules and quartz wool. The catalyst was reduced in-situ for 3 h at 723 K (1 K min$^{-1}$) before use. The feed was introduced into the reactor using an HPLC pump (Lab Alliance-brand Series I; Scientific System, Inc., State College, Pa., USA). Simulated feeds for catalytic experiments were prepared by adding commercial LA, FA and GVL to SBP. The flow of $H_2$ during the reaction (25 cm$^3$(STP)/min) was controlled by a mass flow controller (Brooks Instrument, 5850S; Brooks Instrument, Inc., Hatfield, Pa., USA). The tubular reactor was fitted inside an aluminum block and placed within an insulated furnace (Applied Test Systems, Butler, Pa., USA). Bed temperature was monitored at the reactor wall using a Type K thermocouple (Omega Engineering, Inc., Stamford, Conn., USA) and controlled using a 16A series programmable temperature controller (Love Controls, Inc., Michigan City, Ind., USA). Reactor pressure (35 bar of $H_2$) was controlled using a back pressure regulator (model BP-60; GO Regulator, Inc, Spartanburg, S.C., USA). The reactor effluent flowed into a vapor-liquid separator wherein the liquid product was collected. Gas phase products were analyzed using an in-line pair of gas chromatographs. A GC-2014 (Shimadzu) equipped with an FID was used for analysis of hydrocarbon products in the gas phase, while CO and $CO_2$ were quantified using a GC-8A (Shimadzu) with a TCD using helium as a carrier/reference. Liquid samples were drained from the separator and the concentration of organic species quantified using a GC-2010 (Shimadzu) with an FID. Identification of products was achieved using GC-MS analysis (Shimadzu GCQP-2010

TABLE 6

Effect of temperature and feed composition on LA conversion using Ru—Sn/C with a molar ratio of 3.6:1 Ru:Sn (unless noted) in a flow reactor.

| Entry | Feed (M in SBP) LA | FA | T (K) | WHSV (h$^{-1}$) | LA conversion (%) | GVL rate (mmol min$^{-1}$ g$_{cat}^{-1}$) | LA selectivity (%) GVL | MTHF | Other |
|---|---|---|---|---|---|---|---|---|---|
| 1* | 2 | 2 | 493 | 2.8 | 27 | 0.10 | 90.5 | 0.3 | 9.2 |
| 2 | 2 | 2 | 493 | 1.5 | 46 | 0.09 | 93.4 | 4.3 | 2.3 |
| 3 | 2 | 2 | 513 | 1.2 | 58 | 0.09 | 88.5 | 5.5 | 6.0 |
| 4 | 2 | 2 | 473 | 1.2 | 19 | 0.03 | 91.0 | 1.4 | 6.8 |
| 5 | 0.5 | 0.5 | 493 | 1.2 | 54 | 0.09 | 97.7 | 0.8 | 1.5 |
| 6 | 2 | 0 | 493 | 2.2 | 98 | 0.30 | 95.8 | 3.6 | 0.6 |
| 7 | 2 | 0 | 473 | 2.2 | 52 | 0.16 | 97.5 | 2.5 | 0 |
| 8† | 2 | 2 | 493 | 1.5 | 44 | 0.09 | 92.9 | 4.6 | 2.5 |

*Catalyst 5% Ru/C.
†feed includes 2M GVL

Any number of types of hydrogenation catalysts can be used in the method to accomplish the reduction of LA to GVL. Table 7 shows the results of hydrogenation reactions, LA to GVL, using SBP as the AP, at various reaction temperatures, and using different hydrogenation catalysts.

TABLE 7

LA hydrogenation to GVL in presence of SBP.

| Catalyst | T (C.) | WHSV (h−1) | LA conversion (%) | GVL selectivity (%) | MTHF selectivity (%) | 1,4 pentanediol selectivity (%) | SBP hydrogenation (%) |
|---|---|---|---|---|---|---|---|
| Topsoe | 150 | 0.59 | 21 | 100 | 0 | 0 | 0 |
| Topsoe | 180 | 0.59 | 46 | 99.6 | 0.4 | 0 | 0 |
| Raney Cu | 200 | 1.13 | 95 | 99.5 | 0.1 | 0.4 | 0 |
| Raney Cu | 200 | 1.13 | 15 | 99.9 | 0.1 | 0 | 0 |
| Ru/C | 150 | 0.6 | 97 | 98.2 | 0.2 | 1.6 | 41 |
| Ru/C | 150 | 1.1 | 18 | 99.3 | 0.7 | 0 | 0.6 |
| 3Ru 1Cu | 150 | 0.6 | 22 | 99.5 | 0.5 | 0 | 0.3 |
| 3Ru 1Sn | 150 | 0.6 | 22 | 99.7 | 0.3 | 0 | 0 |
| 3Ru 1Sn | 170 | 0.6 | 43 | 99.4 | 0.6 | 0 | 0 |
| 3Ru 1Sn | 220 | 1.3 | 44 | 97.5 | 2.5 | 0 | 0 |
| 3Ru 1Sn | 240 | 1.3 | 42 | 95.5 | 4.5 | 0 | 0 |

Figure 8:
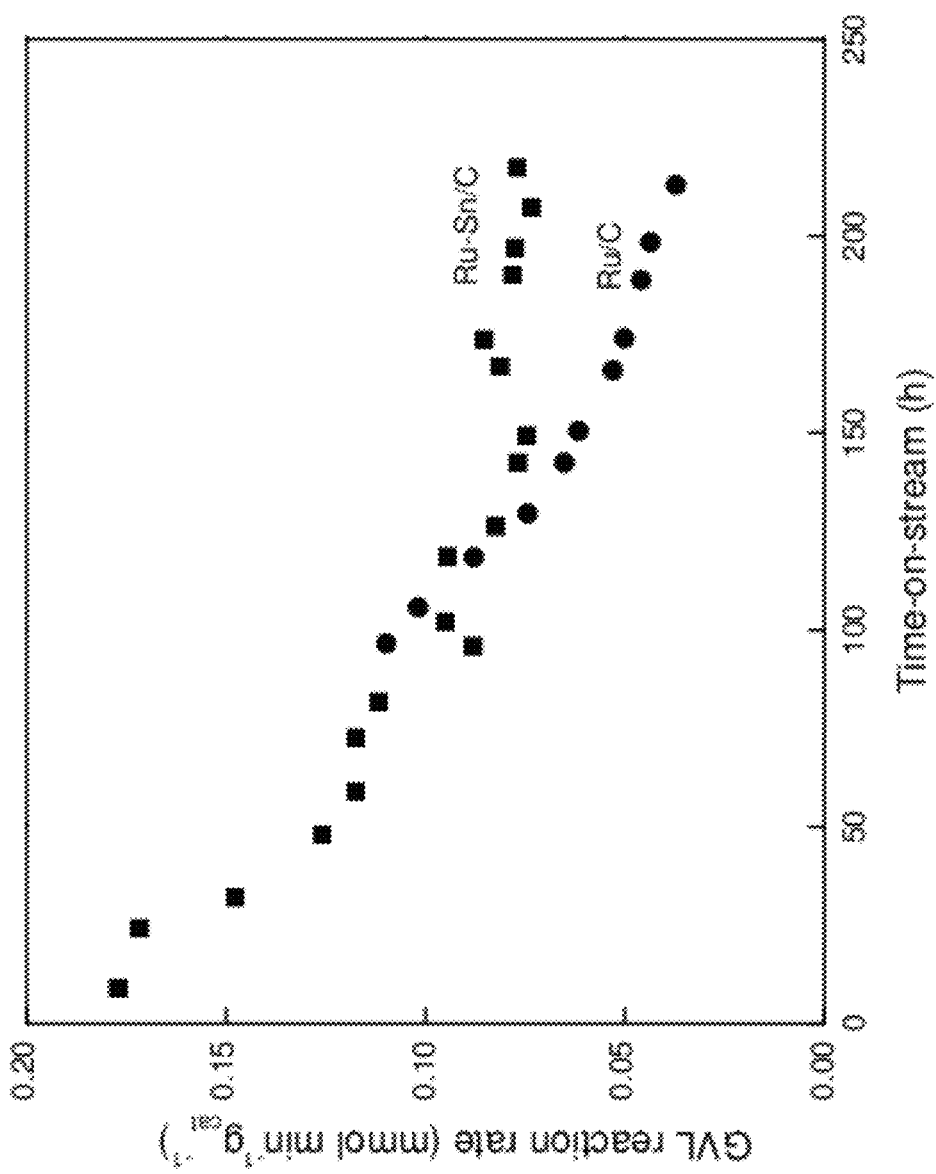
FIG. 8 is a graph depicting production rate of GVL versus time on stream at 493 K and 35 bar ($H_2$). Feed composition is 2 M LA and 2 M FA in SBP with a WHSV of 1.6 $h^{-1}$ for Ru—Sn/C (■) and 2.9 $h^{-1}$ for Ru/C (●).
Figure 9:
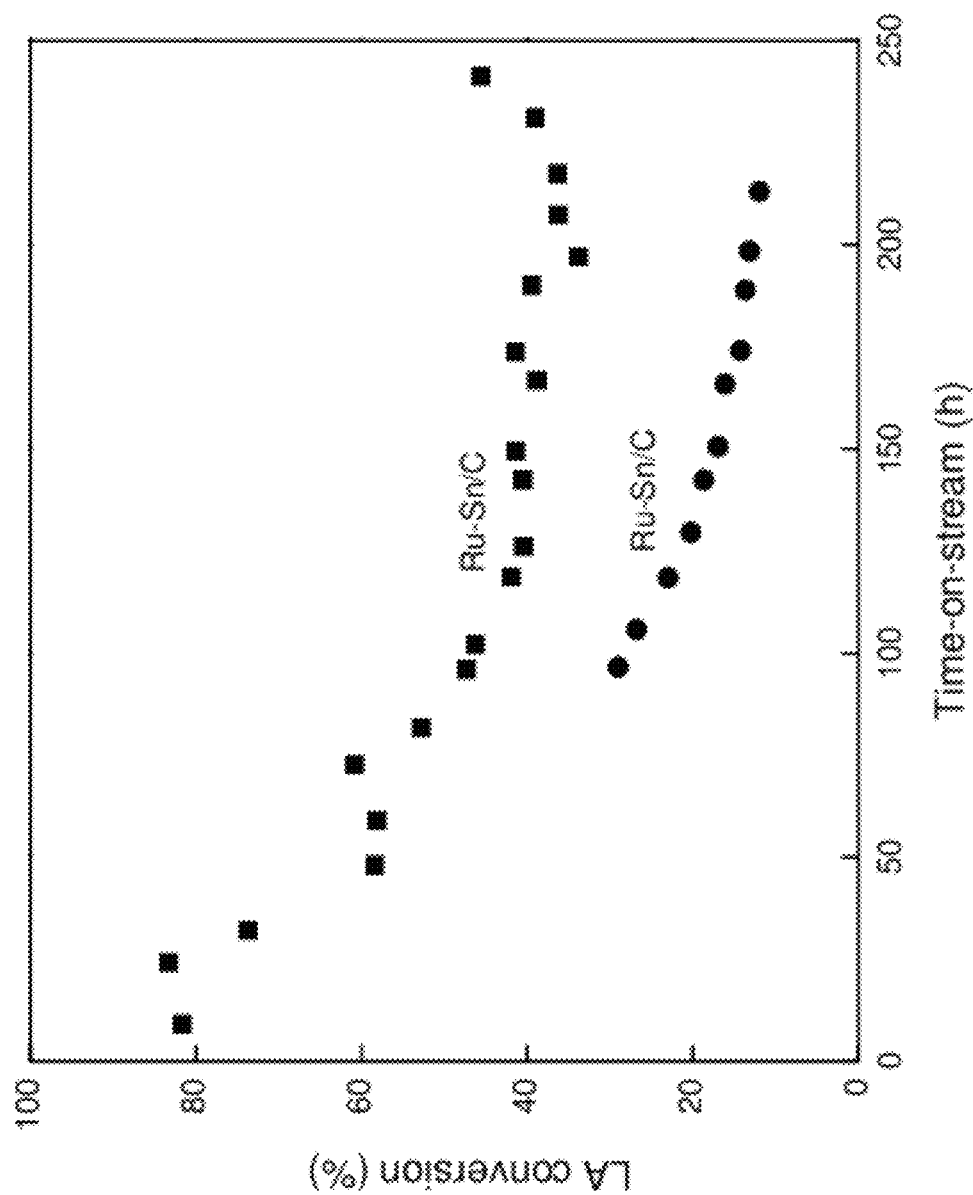
FIG. 9 is a graph depicting LA conversion versus time on stream at 493 K and 35 bar ($H_2$). Feed composition is 2 M LA and 2 M FA in SBP with a WHSV of 1.6 $h^{-1}$ for Ru—Sn/C (■) and 2.9 $h^{-1}$ for Ru/C (●).

FIGS. 8 and 9 illustrate that the Ru—Sn/C catalyst initially undergoes deactivation, during which the rate of GVL production and LA conversion decrease in the first 100 h time on stream. The catalyst then remains stable for more than 200 h. In the case of Ru/C, the catalyst showed continuous deactivation, with the rates of GVL production and LA conversion decreasing continuously after 200 h.

Example 8

Hydrogenation of LA to GVL by Hydrogen Transfer

Hydrogenation of levulinic acid to GVL is carried out by hydrogen transfer using alcohols as hydrogen donors and a metal oxide as $ZrO_2$. The $ZrO_2$ catalyst was prepared by precipitation of $ZrO(NO_3)_2$ with $NH_4OH$ (Aldrich), according to Serrano-Ruiz et al. (*J. Catal.*, 241, (2006), 45-55). Solids were calcined in 60 cm$^3$ (STP)/min flowing air at 723 K for 4 h prior to use in batch experiments. Quantification was performed using a gas chromatograph (Shimadzu GC-2010; Shimadzu Scientific Instruments, Columbia, Md.) equipped with a flame-ionization detector (FID). Identification of products in the liquid phase was performed using a gas chromatograph-mass spectrometer (Shimadzu Corp., GCMS-QP2010S) equipped with a Rxi®-brand SHRXI-5MS capillary column (30 m×0.25 mm×0.25 µm) (Restek Corporation, Bellefonte, Pa.).

Figure 10:
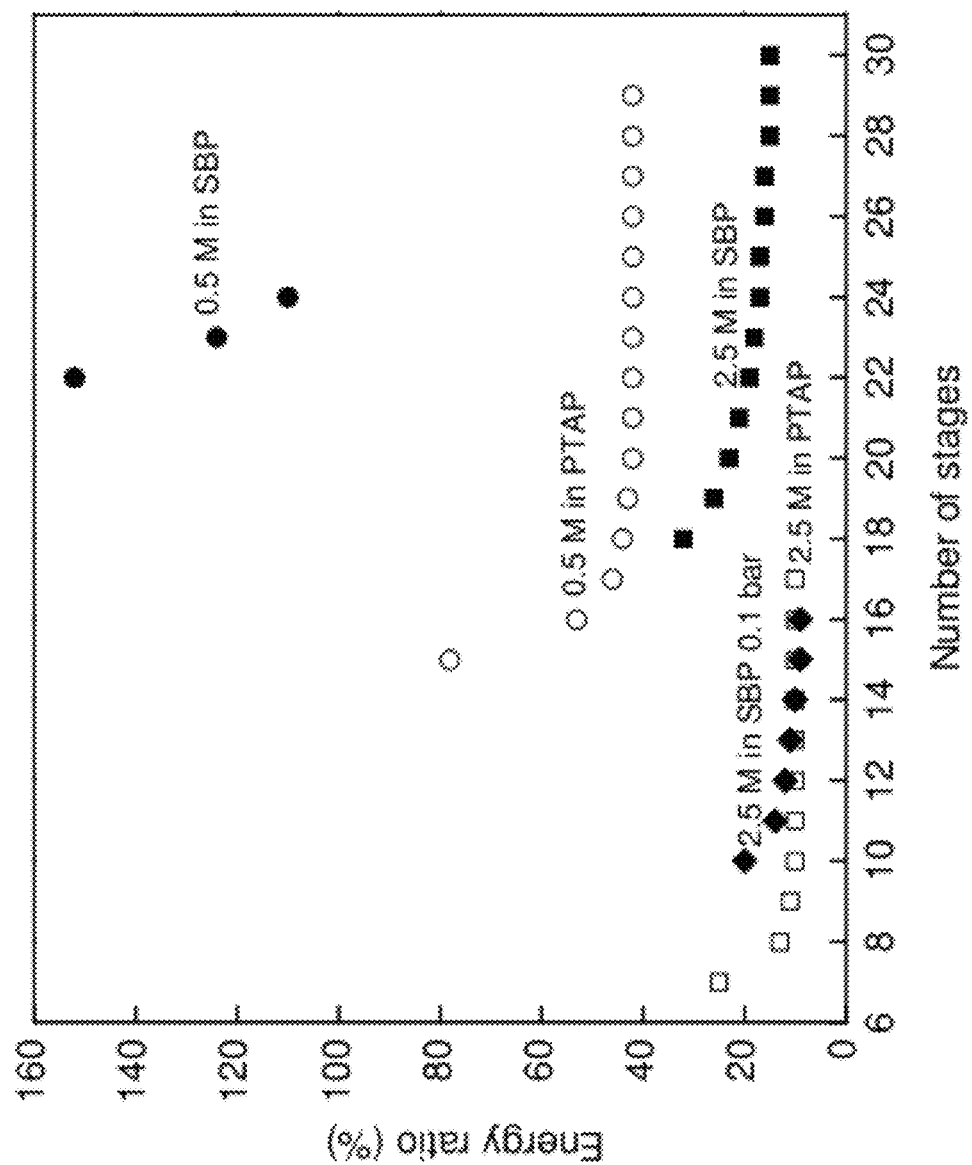
FIG. 10: Energy ratio (defined as percentage of GVL combustion energy) used in the reboiler versus the number of stages in the separation by distillation of GVL from AP at 1 bar. Feed concentration of GVL: 2.5 M in SBP (■), 0.5 M in SBP (●), 2.5 M in PTAP (□), 0.5 M GVL in PTAP (○), and 2.5 M in SBP at 0.1 bar (♦).

The reactions were performed in a 50 mL batch reactor (Parr Instruments). For all experiments, the feed was 5 wt % levulinate ester or LA in a solvent (solvent composition is described in Table 8). $ZrO_2$ was used as the catalyst. Reactor contents were pressurized under 300 psi He prior to heating to the reaction temperature (150° C.). In all cases, SBP was not converted during the reaction and behaved as an inert diluent. Besides GVL, the only other products observed were levulinate esters formed through transesterification or esterification reactions between the reactants and the hydrogen donors. As shown in Table 8, IPA, 2 BuOH, and 2HO are suitable hydrogen donors for these reactions. Also, the conversion of levulinate esters (Ethyl levulinate (EL) or butyl levulinate (BL) to GVL occurs at a higher rate than that for LA to GVL.

brand modeling software (Aspen Technology, Inc., Burlington, Mass., USA) was used to conduct simulations of the distillation column using different feed compositions and alkylphenols. FIG. 10 shows the energy ratio (heat necessary in the reboiler divided by the lower combustion heat of GVL) as indicative of the operational cost, versus the number of stages, as indicative of the capital cost, to recover 95% of the GVL with 95 wt % purity from the feed at 298 K and 1 bar.

Increasing the concentration of GVL in the feed from 0.5 M to 2.5 M considerably reduces the number of stages necessary to achieve separation and the heat required in the reboiler. For example, using 0.5 M GVL in SBP as feed and with 22 stages, the energy ratio is 152%, meaning that 52% more energy is required than is provided by the combustion of the GVL. When the GVL feed concentration is 2.5 M, then the energy ratio is only 19%, and 10 stages are required. Similar reductions in reboiler energy requirements are observed using AP solvents with higher boiling points. For example, the energy ratio is 10% using para-tert-amylphenol (PTAP) as the solvent, a GVL concentration of 2.5 M, and 10 stages. Another option to reduce the reboiler heat and the number of stages is to carry out the distillation under vacuum (0.1 bar), but such operation increases capital and operating costs.

Figure 11:
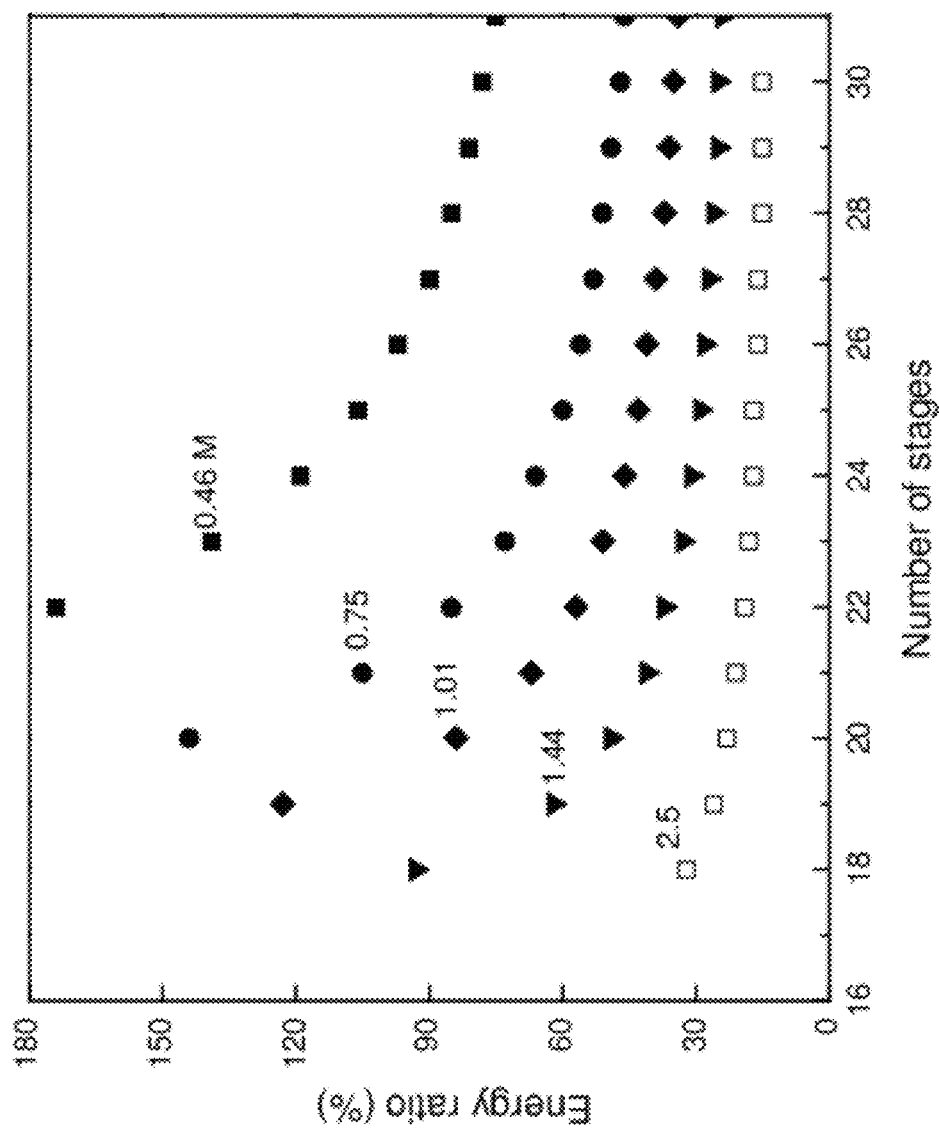
FIG. 11: Energy ratio (defined as percentage of GVL combustion energy) versus number of stages in the separation by distillation of GVL from AP at 1 bar. Feed composition of GVL into distillation column: 0.46 M in SBP (■), 0.75 M in SBP (●), 1.01 M in SBP (♦), 1.44 M in SBP (▼), and 2.5 M in SBP (□).

FIG. 11 shows the simulated decrease in required reboiler heat and number of stages associated with the recycling of the mixture of solvent and final products (i.e., GVL) several times, illustrating how the size of the column and the energy requirements decrease as the GVL concentration increases. For example, after a single cycle, the GVL concentration is 0.44 M and 30 stages are necessary to carry out the separation, with an energy ratio of 78%. After 4 cycles, the GVL concentration has increased to 1.44 M, and with the same number of stages, the energy ratio is just 25%. Additional increases in GVL concentration further reduce the heat requirements and size of the column. Additional energy saving can be achieved if the distillation column is fed directly from the hydrogenation reactor at 493 K, alleviating the need to heat the stream prior to distillation.

REFERENCES

1. E. L. Kunkes et al., *Science* 322, 417 (2008).
2. D. M. Alonso, J. Q. Bond, J. A. Dumesic, *Green Chem.* 12, 1493 (2010).

TABLE 8

Catalytic transfer hydrogenation of levulinate esters and levulinic acid to γ-valerolactone over $ZrO_2$ using various secondary alcohols as the hydrogen donor in the presence of sec-butylphenol.

| H donor | H acceptor | H donor:SBP (g:g) | Time (h) | Catalyst:ester or LA (g:g) | Ester or LA conversion (%) | GVL yield (%)* | GVL formation rate ($\mu mol\,g^{-1}\,min^{-1}$) |
|---|---|---|---|---|---|---|---|
| IPA | EL | 18:1 | 16 | 1:2 | >99 | 86 | — |
| IPA | EL | 8:1 | 16 | 1:2 | >99 | 84 | — |
| IPA | EL | 1:1 | 16 | 1:2 | >99 | 95 | — |
| 2BuOH | BL | 1:1 | 16 | 1:2 | >99 | 83 | — |
| 2BuOH | BL | 1:1 | 8 | 1:5 | 60 | 51 | 27.2 |
| 2BuOH | BL | 1:1 | 4 | 1:5 | 30 | 29 | 31.5 |
| 2-HO | BL | 1:1 | 8 | 1:5 | 39 | 17 | 9.7 |
| IPA | LA | 1:4 | 16 | 1:2 | 34 | 7 | 1.3 |
| IPA | LA | 1:1 | 16 | 1:2 | 69 | 15 | 2.7 |

*Levulinate esters only by-product.

Example 9

Distillation of GVL

A possible final stage of multiple processes described herein is the separation of GVL from the AP, obtaining pure GVL at the top of a distillation column. ASPEN PLUS®-

3. J. J. Bozell, G. R. Petersen, *Green Chem.* 12, 539 (2010).
4. J. J. Bozell, *Science* 329, 522 (2010).
5. J. P. Lange et al., *Angew. Chem. Inter. Ed.* 49, 4479 (2010).
6. F. M. A. Geilen et al., *Angew. Chem. Inter. Ed.* 49, 5510 (2010).
7. H. Heeres et al., *Green Chem.* 11, 1247 (2009).
8. H. Mehdi et al., *Top. Catal.* 48, 49 (2008).

9. J. J. Bozell et al., *Resour. Conserv. Recy.* 28, 227 (2000).
10. L. Deng, J. Li, D. M. Lai, Y. Fu, Q. X. Guo, *Angew. Chem. Int. Ed.* 48, 6529 (2009).
11. Z. P. Yan, L. Lin, S. J. Liu, *Energ. fuel* 23, 3853 (2009).
12. I. T. Horvath, H. Mehdi, V. Fabos, L. Boda, L. T. Mika, *Green Chem.* 10, 238 (2008).
13. J. Q. Bond, D. M. Alonso, D. Wang, R. M. West, J. A. Dumesic, *Science* 327, 1110 (2010).
14. J. P. Lange, J. Z. Vestering, R. J. Haan, *Chem. Commun.*, 3488 (2007).
15. D. Fegyverneki, L. Orha, G. Lang, I. T. Horvath, *Tetrahedron* 66, 1078 (2010).
16. S. W. Fitzpatrick. U.S. Pat. No. 5,608,105 (1997).
17. J. C. Serrano-Ruiz, D. J. Braden, R. M. West, J. A. Dumesic, *Appl. Catal. B-Environ.* 100, 184 (2010).
18. D. J. Braden, thesis, UW-Madison (2010).
19. Kirk-Othmer Encyclopedia of Chemical Technology (Ed Wiley, New York 2000) vol. 2, pp. 203-232.
20. B. A. Riguetto et al., *Appl. Catal. Gen.* 318, 70 (2007).
21. J. Springerova, P. Kacer, L. Cerveny, *Res. Chem. Intermediat.* 31, 785 (2005).
22. See figures and examples for further details
23. J. Horvat, B. Klaic, B. Metelko, V. Sunjic, *Tetrahedron Lett.* 26, 2111 (1985).
24. C. Fellay, P. J. Dyson, G. Laurenczy, *Angew. Chem. Int. Edit.* 47, 3966 (2008).
25. M. R. Prairie, A. Renken, J. G. Highfield, K. R. Thampi, M. Gratzel, *J. Catal.* 129, 130 (1991).
26. G. W. Huber, J. W. Shabaker, J. A. Dumesic, *Science* 300, 2075 (2003).
27. C. G. Liu, C. E. Wyman, *Ind. Eng. Chem. Resear.* 42, 5409 (2003).

What is claimed is:

1. A process to make furan derivative compounds, the process comprising:
    dehydrating a feedstock solution comprising a carbohydrate, in the presence of an acid catalyst, in a reaction vessel containing a biphasic reaction medium comprising an aqueous reaction solution, and acid catalyst, and a substantially immiscible organic extraction solution comprising at least one alkylphenol, wherein furan derivatives formed in the aqueous reaction solution are extracted into the organic extraction solution.

2. The process of Claim 1, wherein the acid catalyst is a mineral acid.

3. The process of Claim 1, wherein the furan derivative formed is furfural.

4. The method of Claim 3, further comprising isolating or purifying the furfural.

5. The method of Claim 3, further comprising hydrogenating the furfural into furfuryl alcohol in the presence of at least one alkylphenol.

6. The method of Claim 5, further comprising isolating or purifying the furfuryl alcohol.

7. The method of Claim 5, further comprising converting the furfuryl alcohol into levulinic acid in the presence of at least one alkylphenol.

8. The method of Claim 7, further comprising isolating or purifying the levulinic acid.

9. The method of Claim 7, further comprising reducing the levulinic acid into γ-valerolactone in the presence of at least one alkylphenol.

10. The method of Claim 9, further comprising recycling a portion or all of the γ-valerolactone into the vessel in which the levulinic acid was produced in the presence of at least one alkylphenol.

11. The method of Claim 5, further comprising converting the furfuryl alcohol into levulinic acid esters in the presence of at least one alkylphenol.

12. The method of Claim 11, further comprising isolating or purifying the levulinic acid esters.

13. The method of Claim 11, further comprising reducing the levulinic acid esters into γ-valerolactone in the presence of at least one alkylphenol.

14. The method of Claim 13, further comprising recycling a portion or all of the γ-valerolactone into the vessel in which the levulinic acid esters were produced in the presence of at least one alkylphenol.

15. The process of Claim 1, wherein the furan derivative formed is hydroxymethylfurfural (HMF).

16. The method of Claim 15, further comprising isolating or purifying the HMF.

17. The method of Claim 15, further comprising converting the HMF to an HMF-ether.

18. The method of Claim 17, further comprising isolating or purifying the HMF-ether.

19. The method of Claim 15, further comprising converting the HMF to levulinic acid or levulinate ester.

20. The method of Claim 19, further comprising isolating or purifying the levulinic acid or levulinate ester.

21. The method of Claim 19, further comprising converting the levulinic acid or levulinate ester to GVL.

22. The method of Claim 21, further comprising isolating or purifying the GVL.

23. The method of any one of claims 1 to 22, wherein the organic extraction solution comprises an alkylphenol selected from the group consisting of:

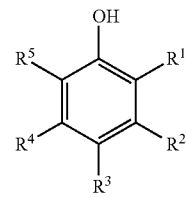

wherein $R^1$-$R^5$ are independently selected from the group consisting of hydrogen, hydroxyl, esters, ethers, carboxylic acids, and $C_1$-$C_{24}$ linear, branched, or cyclic alkyl or alkene, provided that at least one of $R^1$-$R^5$ is an alkyl group.

24. A method of making levulinic acid, the method comprising:
    (a) dehydrating a feedstock solution comprising a carbohydrate in an aqueous reaction solution, in the presence of an acid catalyst, to yield furfural;
    (b) in a first reaction vessel, extracting the aqueous reaction solution of step (a) with a substantially immiscible organic extraction solution comprising at least one alkylphenol, wherein furfural from step (a) is extracted into the organic extraction solution;
    (c) hydrogenating furfural from step (b) into furfuryl alcohol; and
    (d) converting furfuryl alcohol from step (c) into levulinic acid or a levulinate ester in the presence of an alkylphenol.

25. The method of Claim 24, further comprising recycling organic extraction solution from step (d) into the first reaction vessel of step (b).

26. The method of Claim 24, further comprising isolating the levulinic acid or levulinate ester.

27. The method of Claim 24, further comprising:
(e) hydrogenating at least a portion of the levulinic acid or levulinate ester of step (d) into γ-valerolactone.

28. The method of Claim 27, further comprising recycling at least a portion of the γ-valerolactone from step (e) into the second reaction vessel of step (d).

29. The method of any one of claims 24 to 28, wherein the organic extraction solution comprises an alkylphenol selected from the group consisting of:

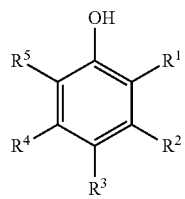

wherein $R^1$-$R^5$ are independently selected from the group consisting of hydrogen, hydroxyl esters, ethers, carboxylic acids, and $C_1$-$C_{24}$ linear, branched, or cyclic alkyl or alkene, provided that at least one of $R^1$-$R^5$ is an alkyl group.

30. A method of making levulinic acid, the method comprising:
(a) dehydrating a feedstock solution comprising a carbohydrate in an aqueous reaction solution, in the presence of an acid catalyst, to yield hydroxymethylfurfural (HMF);
(b) in a first reaction vessel, extracting the aqueous reaction solution of step (a) with a substantially immiscible organic extraction solution comprising at least one alkylphenol, wherein HMF from step (a) is extracted into the organic extraction solution;
(c) converting HMF from step (b) into levulinic acid or a levulinic acid ester; and
(d) in a second reaction vessel, extracting the levulinic acid or levulinic acid ester from step (c) into an organic extraction solution comprising at least one alkylphenol.

31. The method of claim 30, wherein the organic extraction solution comprises an alkylphenol selected from the group consisting of:

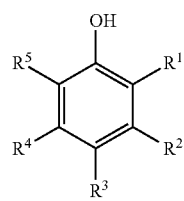

wherein $R^1$-$R^5$ are independently selected from the group consisting of hydrogen, hydroxyl esters, ethers, carboxylic acids, and $C_1$-$C_{24}$ linear, branched, or cyclic alkyl or alkene, provided that at least one of $R^1$-$R^5$ is an alkyl group.

* * * * *